US012639808B2

(12) United States Patent

Sue et al.

(10) Patent No.: US 12,639,808 B2

(45) Date of Patent: May 26, 2026

(54) SYSTEMS AND METHODS FOR PROCESSING ELECTRONIC MEDICAL IMAGES TO OPTIMIZE A REVIEW ORDER OF PATHOLOGY CASES

(71) Applicant: PAIGE.AI, Inc., New York, NY (US)

(72) Inventors: Jillian Sue, New York, NY (US); Sam Seymour, Portland, OR (US)

(73) Assignee: Paige.AI, Inc., New York, NY (US)

( * ) Notice: Subject to any disclaimer, the term of this patent is extended or adjusted under 35 U.S.C. 154(b) by 717 days.

(21) Appl. No.: 17/936,626

(22) Filed: Sep. 29, 2022

(65) Prior Publication Data

US 2023/0196562 A1 Jun. 22, 2023

Related U.S. Application Data

(60) Provisional application No. 63/290,479, filed on Dec. 16, 2021.

(51) Int. Cl.

| | |
|---|---|
| *G06T 7/00* | (2017.01) |
| *G06F 18/2132* | (2023.01) |
| *G06V 10/25* | (2022.01) |
| *G06V 10/764* | (2022.01) |
| *G16H 10/40* | (2018.01) |

(52) U.S. Cl.

CPC ...... *G06T 7/0012* (2013.01); *G06F 18/21322* (2023.01); *G06V 10/25* (2022.01); *G06V 10/765* (2022.01); *G16H 10/40* (2018.01); *G06F 18/21326* (2023.01); *G06T 2207/30024* (2013.01); *G06T 2207/30168* (2013.01)

(58) Field of Classification Search

None

See application file for complete search history.

(56) References Cited

U.S. PATENT DOCUMENTS

| | | | | |
|---|---|---|---|---|
| 10,475,182 | B1 * | 11/2019 | Chilamkurhy | ......... G06V 10/82 |
| 10,504,227 | B1 * | 12/2019 | Chilamkurhy | ......... G06N 3/045 |
| 10,937,164 | B2 * | 3/2021 | Steigauf | ................ G06T 7/0014 |
| 11,210,787 | B1 * | 12/2021 | Godrich | ................ G16H 30/40 |
| 11,508,065 | B2 * | 11/2022 | Putha | ................... G06N 3/0464 |
| 2017/0270666 | A1 * | 9/2017 | Barnes | ................ G06V 20/698 |
| 2019/0228524 | A1 * | 7/2019 | Chen | .................. G06F 18/2148 |
| 2020/0381122 | A1 * | 12/2020 | Godrich | ................ G16H 30/40 |
| 2021/0073984 | A1 * | 3/2021 | Locke | .................. G06T 7/0012 |
| 2021/0350166 | A1 * | 11/2021 | Sue | ........................ G16H 30/40 |

(Continued)

*Primary Examiner* — Tahmina N Ansari

(74) *Attorney, Agent, or Firm* — Bookoff McAndrews, PLLC

(57) ABSTRACT

Systems and methods are described herein for processing electronic medical images to optimize a review order of pathology cases. For example, a plurality of variables and one or more constraints may be received along with a plurality of pathology cases. Each case of the plurality of pathology cases may include one or more medical images of at least one pathology specimen associated with a patient. The medical images from each case, the plurality of variables, and the one or more constraints may be provided as input to a trained system. A sequential order for user review of the plurality of cases to optimize one or more of the plurality of variables based on the one or more constraints may be received as output of the trained system. Each case of the plurality of cases may be automatically provided to a user for review according to the sequential order.

20 Claims, 12 Drawing Sheets

(56) References Cited

U.S. PATENT DOCUMENTS

| | | | |
|---|---|---|---|
| 2023/0196562 A1* | 6/2023 | Sue ...................... | G06V 10/765 |
| | | | 382/128 |
| 2025/0273324 A1* | 8/2025 | Abramoff .............. | G06V 10/87 |

* cited by examiner

300

302 RECEIVE TRAINING DATASETS

304 TRAIN THE SYSTEM TO BE CONFIGURED TO DETERMINE A CASE ORDER THAT OPTIMIZES ONE OR MORE OF A PLURALITY OF VARIABLES GIVEN ONE OR MORE CONSTRAINTS IN A CLINICAL SETTING

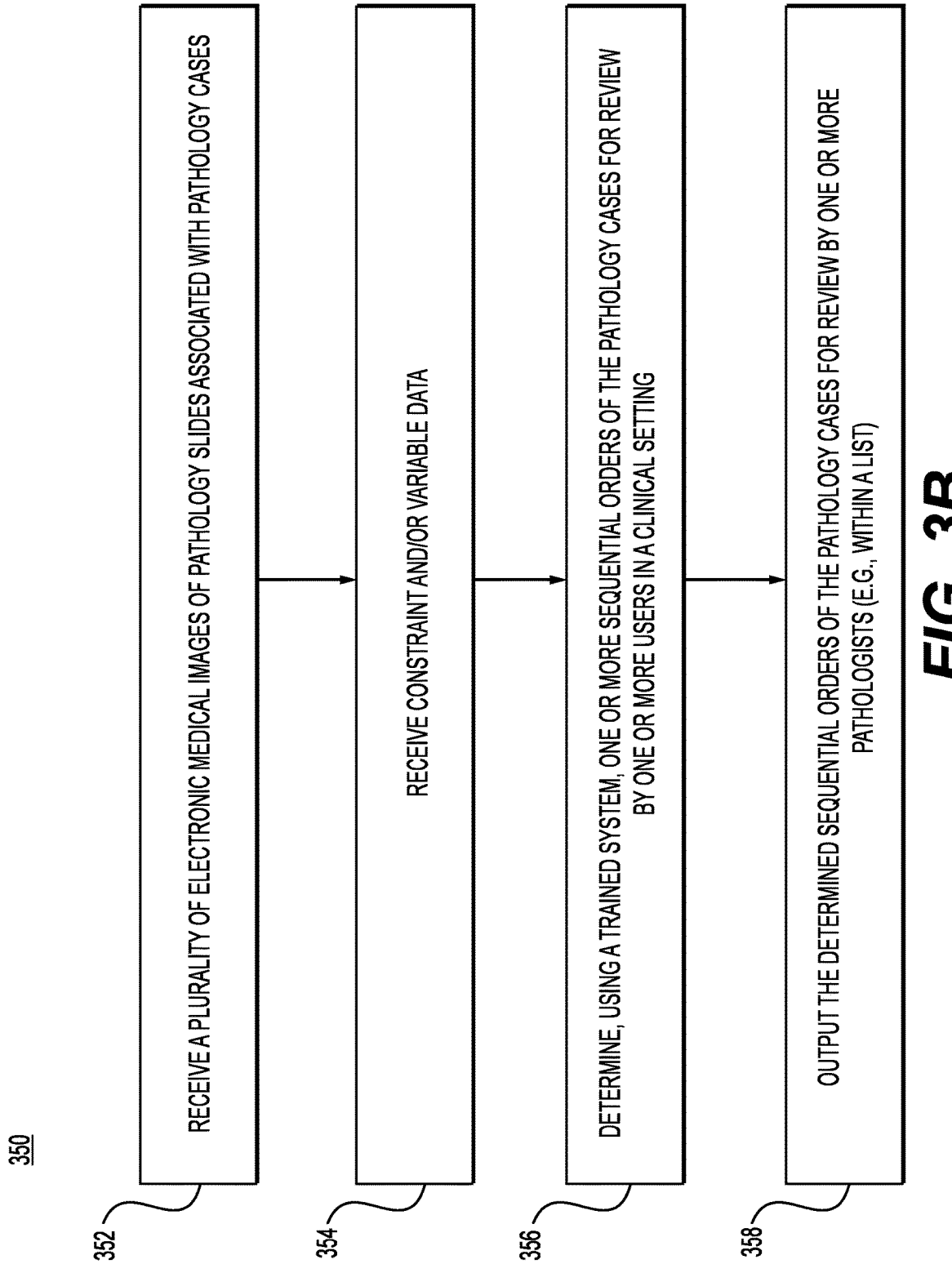

350

352 — RECEIVE A PLURALITY OF ELECTRONIC MEDICAL IMAGES OF PATHOLOGY SLIDES ASSOCIATED WITH PATHOLOGY CASES

354 — RECEIVE CONSTRAINT AND/OR VARIABLE DATA

356 — DETERMINE, USING A TRAINED SYSTEM, ONE OR MORE SEQUENTIAL ORDERS OF THE PATHOLOGY CASES FOR REVIEW BY ONE OR MORE USERS IN A CLINICAL SETTING

358 — OUTPUT THE DETERMINED SEQUENTIAL ORDERS OF THE PATHOLOGY CASES FOR REVIEW BY ONE OR MORE PATHOLOGISTS (E.G., WITHIN A LIST)

402 RECEIVE TRAINING DATASETS

404 TRAIN THE SYSTEM TO BE CONFIGURED TO DETERMINE A CASE ORDER THAT OPTIMIZES ONE OR MORE OF A PLURALITY OF VARIABLES GIVEN ONE OR MORE CONSTRAINTS IN A RESEARCH SETTING

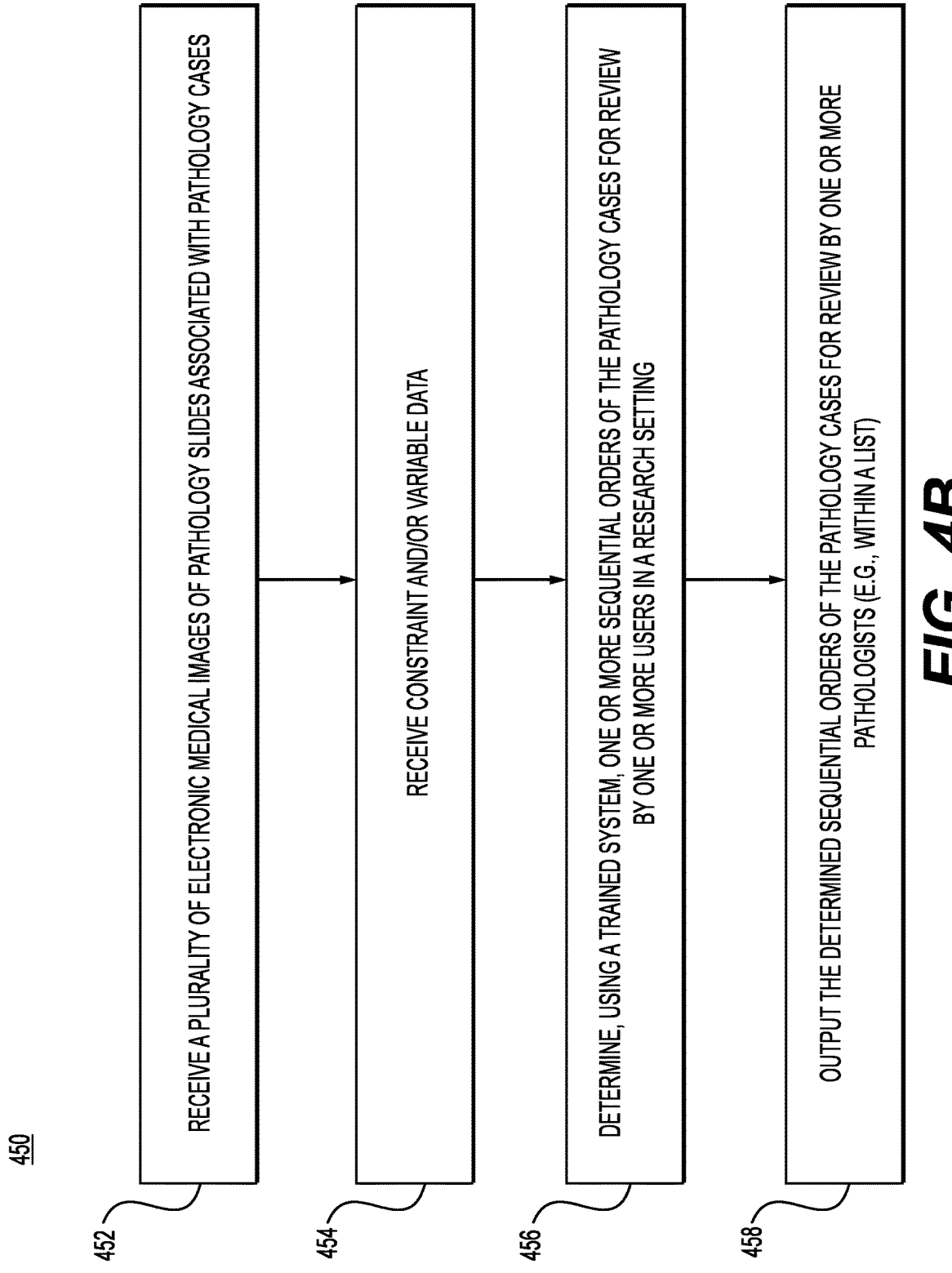

450

452 — RECEIVE A PLURALITY OF ELECTRONIC MEDICAL IMAGES OF PATHOLOGY SLIDES ASSOCIATED WITH PATHOLOGY CASES

454 — RECEIVE CONSTRAINT AND/OR VARIABLE DATA

456 — DETERMINE, USING A TRAINED SYSTEM, ONE OR MORE SEQUENTIAL ORDERS OF THE PATHOLOGY CASES FOR REVIEW BY ONE OR MORE USERS IN A RESEARCH SETTING

458 — OUTPUT THE DETERMINED SEQUENTIAL ORDERS OF THE PATHOLOGY CASES FOR REVIEW BY ONE OR MORE PATHOLOGISTS (E.G., WITHIN A LIST)

*FIG. 4B*

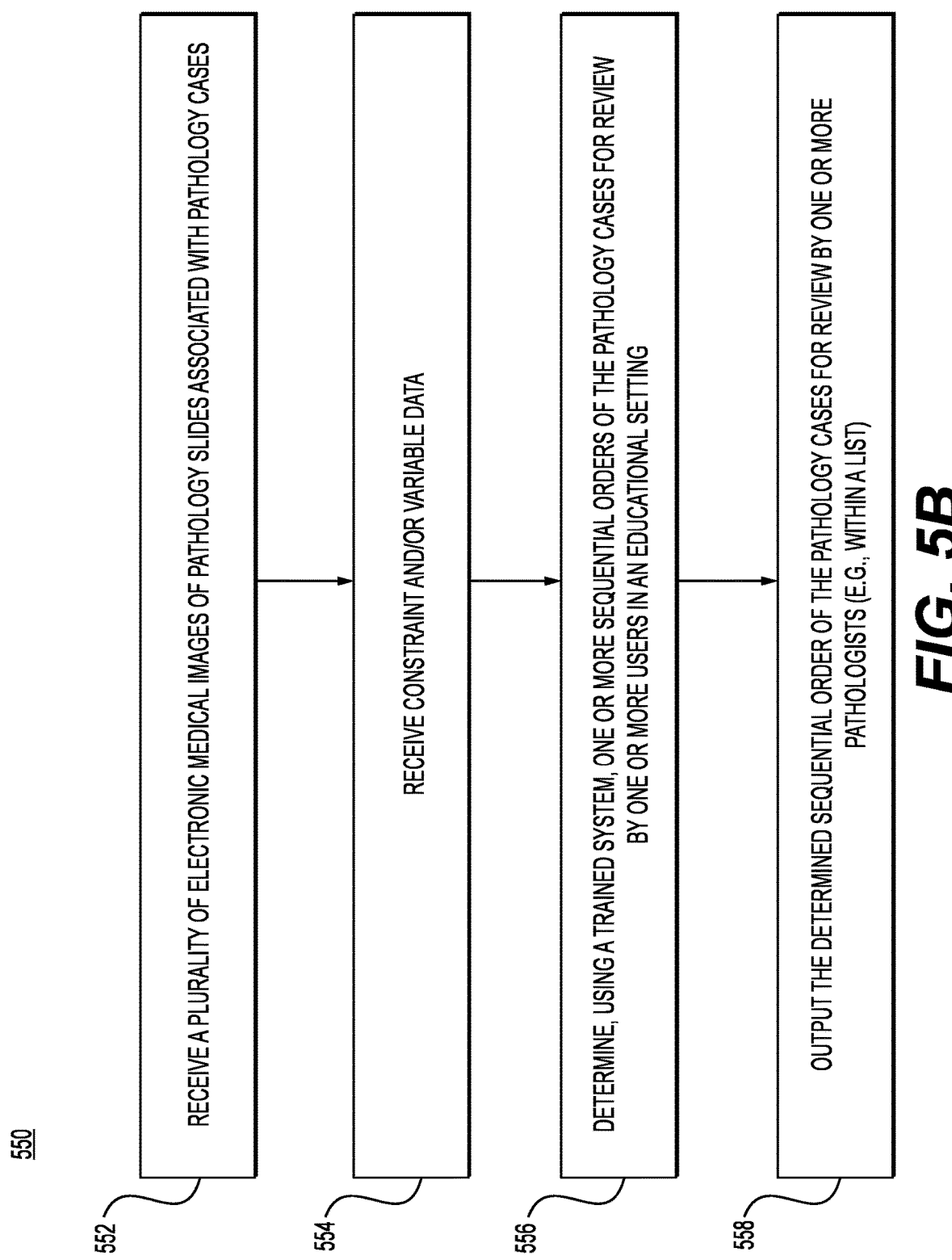

550

552 — RECEIVE A PLURALITY OF ELECTRONIC MEDICAL IMAGES OF PATHOLOGY SLIDES ASSOCIATED WITH PATHOLOGY CASES

554 — RECEIVE CONSTRAINT AND/OR VARIABLE DATA

556 — DETERMINE, USING A TRAINED SYSTEM, ONE OR MORE SEQUENTIAL ORDERS OF THE PATHOLOGY CASES FOR REVIEW BY ONE OR MORE USERS IN AN EDUCATIONAL SETTING

558 — OUTPUT THE DETERMINED SEQUENTIAL ORDER OF THE PATHOLOGY CASES FOR REVIEW BY ONE OR MORE PATHOLOGISTS (E.G., WITHIN A LIST)

*FIG. 5B*

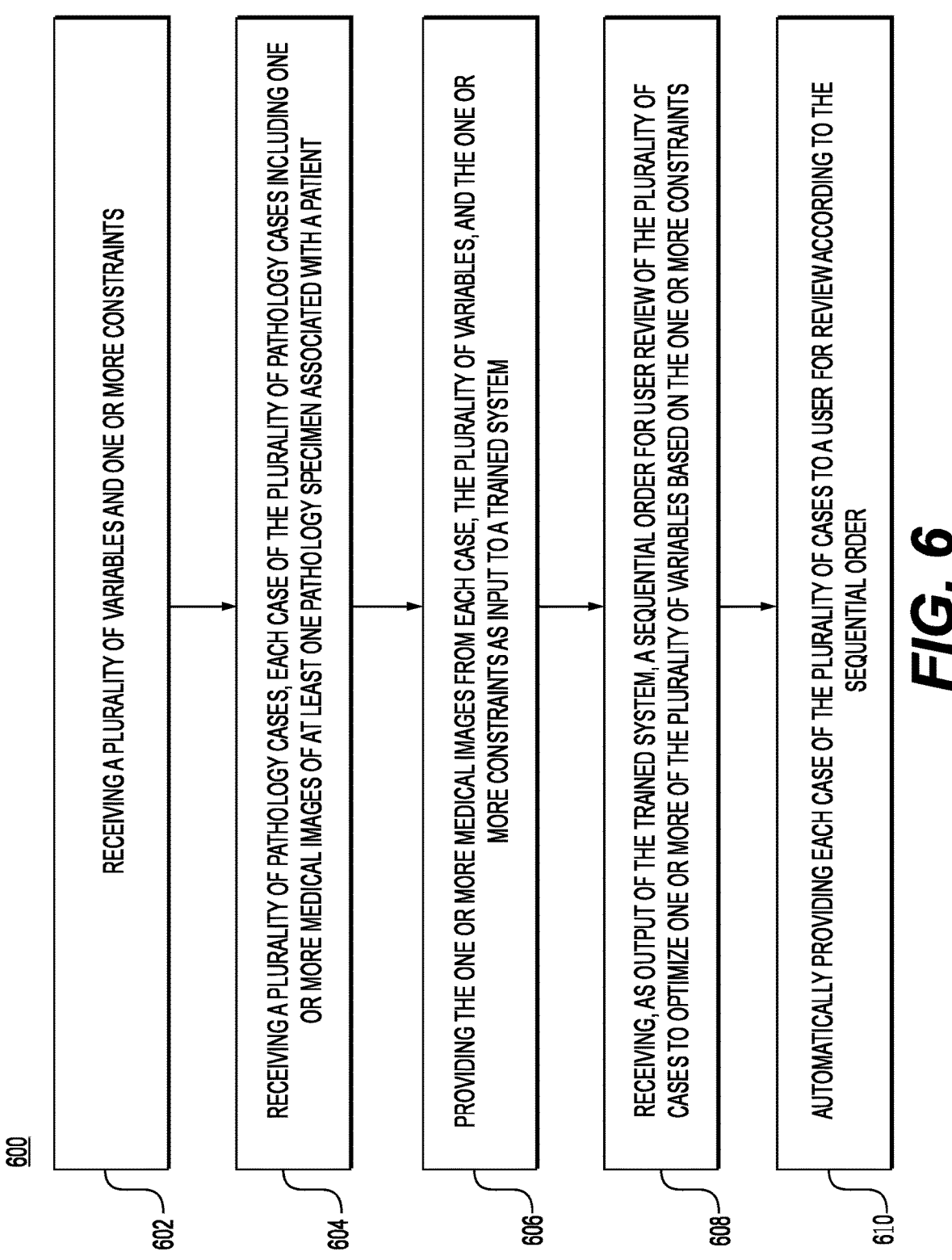

600

602 — RECEIVING A PLURALITY OF VARIABLES AND ONE OR MORE CONSTRAINTS

604 — RECEIVING A PLURALITY OF PATHOLOGY CASES, EACH CASE OF THE PLURALITY OF PATHOLOGY CASES INCLUDING ONE OR MORE MEDICAL IMAGES OF AT LEAST ONE PATHOLOGY SPECIMEN ASSOCIATED WITH A PATIENT

606 — PROVIDING THE ONE OR MORE MEDICAL IMAGES FROM EACH CASE, THE PLURALITY OF VARIABLES, AND THE ONE OR MORE CONSTRAINTS AS INPUT TO A TRAINED SYSTEM

608 — RECEIVING, AS OUTPUT OF THE TRAINED SYSTEM, A SEQUENTIAL ORDER FOR USER REVIEW OF THE PLURALITY OF CASES TO OPTIMIZE ONE OR MORE OF THE PLURALITY OF VARIABLES BASED ON THE ONE OR MORE CONSTRAINTS

610 — AUTOMATICALLY PROVIDING EACH CASE OF THE PLURALITY OF CASES TO A USER FOR REVIEW ACCORDING TO THE SEQUENTIAL ORDER

FIG. 6

SYSTEMS AND METHODS FOR PROCESSING ELECTRONIC MEDICAL IMAGES TO OPTIMIZE A REVIEW ORDER OF PATHOLOGY CASES

RELATED APPLICATION

This application claims priority to U.S. Provisional Application No. 63/290,479 filed Dec. 16, 2021, the entire disclosure of which is hereby incorporated herein by reference in its entirety.

FIELD OF THE DISCLOSURE

Various embodiments of the present disclosure pertain generally to systems and methods for image processing. More specifically, particular embodiments of the present disclosure relate to systems and methods for image processing to determine case optimization.

BACKGROUND

In the field of pathology, with a manual workflow, a pathologist reviews cases primarily based on the order in which the physical slide trays are stacked on their desk. During manual workflow, there may be some cases marked with physical indicators such as "STAT" that require urgent review, and those are pulled out for first review. With a digital workflow, the pathologist has access to a digital worklist or laboratory information system that notes the status of different cases, which ones are assigned to them, and which are pending more information, for example. However, prioritization of these assigned cases for review can be time consuming and inconsistent.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for processing electronic medical images. In one aspect, a computer-implemented method for processing electronic medical images to optimize a review order of pathology cases is disclosed. The method may comprise receiving a plurality of variables and one or more constraints, receiving a plurality of pathology cases, each case of the plurality of pathology cases including one or more medical images of at least one pathology specimen associated with a patient, providing the one or more medical images from each case, the plurality of variables, and the one or more constraints as input to a trained system, receiving, as output of the trained system, a sequential order for user review of the plurality of cases to optimize one or more of the plurality of variables based on the one or more constraints, and automatically providing each case of the plurality of cases to a user for review according to the sequential order.

The trained system may determine a plurality of potential sequential orders and a score for each of the plurality of potential sequential orders indicating a level of optimization of the one or more of the plurality of variables, and the sequential order provided as output is one of the plurality of potential sequential orders having the highest score.

When at least a first variable and a second variable of the plurality of variables are to be optimized, the trained system may determine a first score for the first variable and a second score for the second variable for each of the plurality of potential sequential orders, and the sequential order provided as output may be one of the plurality of potential sequential orders having a maximized overall score based on the first score and the second score.

The one or more of the plurality of variables to be optimized may be user-selected variables. The trained system may be a trained machine learning system or a trained rules-based system.

The method may further comprise receiving, as output from a trained machine learning system configured to process the one or more medical images from each case of the plurality of pathology cases to determine one or more characteristics of the medical images, the determined one or more characteristics of the medical images, and providing the determined one or more characteristics of the medical images as further input to the trained system, the determined one characteristics including a case complexity, a case type, a number of areas of interest per medical image or per case, an amount of tissue per medical image, an image quality.

The method may further comprise receiving one or more additional pathology cases, each case of the one or more additional pathology cases including one or more medical images of at least one pathology specimen associated with a patient, providing the one or more medical images from each of the one or more additional pathology cases as further input to the trained system, and receiving, as output of the trained system, an updated sequential order.

The trained system may be further configured to assign a subset of the plurality of cases to each of a plurality of users, and the sequential order received as output from the trained system includes a sequential order for user review of each subset of the plurality of cases.

The method may further comprise generating a notification to prompt a user to take one or more breaks to increase optimization of one or more of the variables based on information received from the training system.

Automatically providing each case of the plurality of cases to the user for review according to the sequential order may comprise automatically navigating from an initial case to a subsequent case according to the sequential order based on an indication that a review of the initial case is completed.

The indication may be an input received from the user or an event associated with case review completion that is automatically detected.

The method may further comprise monitoring for values associated with the plurality of variables as the user is reviewing the plurality of cases, and providing the values to the trained system, wherein the trained system is re-trained based on the values for future optimizations.

According to certain aspects of the present disclosure, systems and methods are disclosed for processing electronic medical images. In another aspect, a system for processing electronic digital medical images may comprise at least one memory storing instructions and at least one processor configured to execute the instructions to perform operations. The at least one processor may comprise receiving a plurality of variables and one or more constraints, receiving a plurality of pathology cases, each case of the plurality of pathology cases including one or more medical images of at least one pathology specimen associated with a patient, providing the one or more medical images from each case, the plurality of variables, and the one or more constraints as input to a trained system, receiving, as output of the trained system, a sequential order for user review of the plurality of cases to optimize one or more of the plurality of variables based on the one or more constraints; and automatically providing each case of the plurality of cases to a user for review according to the sequential order.

The trained system may determine a plurality of potential sequential orders and a score for each of the plurality of potential sequential orders indicating a level of optimization of the one or more of the plurality of variables. The sequential order provided as output may be one of the plurality of potential sequential orders having the highest score.

When at least a first variable and a second variable of the plurality of variables are to be optimized, the trained system may determine a first score for the first variable and a second score for the second variable for each of the plurality of potential sequential orders, and the sequential order provided as output is one of the plurality of potential sequential orders having a maximized overall score based on the first score and the second score.

The one or more of the plurality of variables to be optimized may be user-selected variables. The trained system may be a trained machine learning system or a trained rules-based system.

The system may further comprise receiving, as output from a trained machine learning system configured to process the one or more medical images from each case of the plurality of pathology cases to determine one or more characteristics of the medical images, the determined one or more characteristics of the medical images, and providing the determined one or more characteristics of the medical images as further input to the trained system, the determined one characteristics including a case complexity, a case type, a number of areas of interest per medical image or per case, an amount of tissue per medical image, an image quality.

According to certain aspects of the present disclosure, systems and methods are disclosed for processing electronic medical images. In another aspect, a non-transitory computer-readable medium storing instructions that, when executed by a processor, perform operations processing electronic digital medical images, is disclosed. The operations may include receiving a plurality of variables and one or more constraints, receiving a plurality of pathology cases, each case of the plurality of pathology cases including one or more medical images of at least one pathology specimen associated with a patient, providing the one or more medical images from each case, the plurality of variables, and the one or more constraints as input to a trained system, receiving, as output of the trained system, a sequential order for user review of the plurality of cases to optimize one or more of the plurality of variables based on the one or more constraints, and automatically providing each case of the plurality of cases to a user for review according to the sequential order.

The trained system may determine a plurality of potential sequential orders and a score for each of the plurality of potential sequential orders indicating a level of optimization of the one or more of the plurality of variables. The sequential order provided as output may be one of the plurality of potential sequential orders having the highest score.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 3B is a flowchart illustrating an example method for using a trained system to determine case order optimization in a clinical context, according to one or more exemplary embodiments herein.

FIG. 4B is a flowchart illustrating an example method for using a trained system to determine case order optimization in a research context, according to one or more exemplary embodiments herein.

FIG. 5B is a flowchart illustrating an example method for using a trained system to determine case order optimization in an educational context, according to one or more exemplary embodiments herein.

FIG. 6 is a flowchart illustrating an example method for optimizing the order of cases displayed to one or more users.

DESCRIPTION OF THE EMBODIMENTS

Figure 1A:
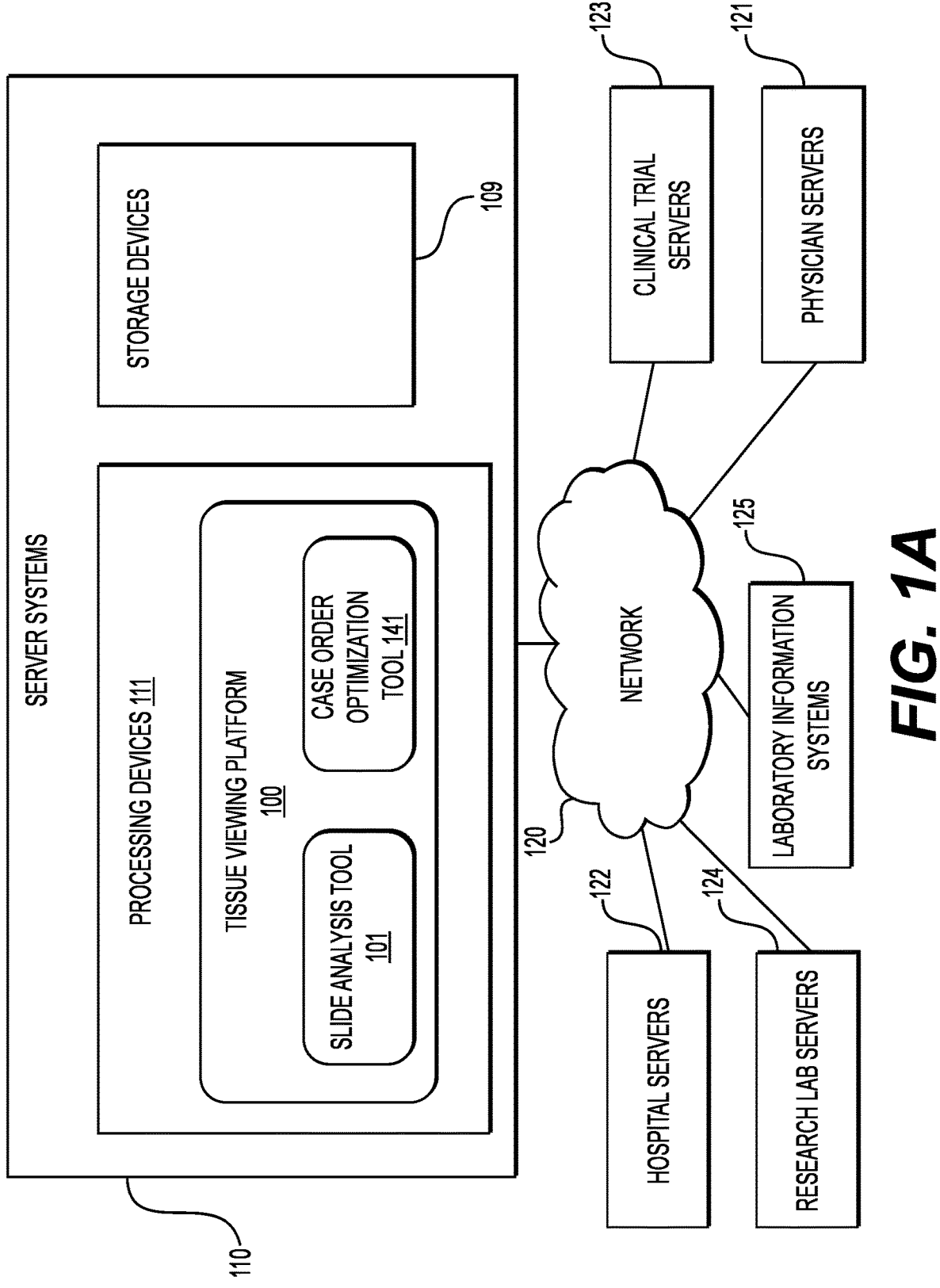
FIG. 1A illustrates an exemplary block diagram of a system and network for processing images to determine an optimal case order, according to techniques presented herein.

Reference will now be made in detail to the exemplary embodiments of the present disclosure, examples of which are illustrated in the accompanying drawings. Wherever possible, the same reference numbers will be used throughout the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as mandatory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a"

and "an" herein do not denote a limitation of quantity, but rather denote the presence of one or more of the referenced items.

As used herein, a "machine learning model" generally encompasses instructions, data, and/or a model configured to receive input, and apply one or more of a weight, bias, classification, or analysis on the input to generate an output. The output may include, for example, a classification of the input, an analysis based on the input, a design, process, prediction, or recommendation associated with the input, or any other suitable type of output. A machine learning model is generally trained using training data, e.g., experiential data and/or samples of input data, which are fed into the model in order to establish, tune, or modify one or more aspects of the model, e.g., the weights, biases, criteria for forming classifications or clusters, or the like. Deep learning techniques may also be employed. Aspects of a machine learning model may operate on an input linearly, in parallel, via a network (e.g., a neural network), or via any suitable configuration.

The execution of the machine learning model may include deployment of one or more machine learning techniques, such as linear regression, logistical regression, random forest, gradient boosted machine (GBM), deep learning, and/or a deep neural network. Supervised and/or unsupervised training may be employed. For example, supervised learning may include providing training data and labels corresponding to the training data, e.g., as ground truth. Unsupervised approaches may include clustering, classification or the like. K-means clustering or K-Nearest Neighbors may also be used, which may be supervised or unsupervised. Combinations of K-Nearest Neighbors and an unsupervised cluster technique may also be used. Any suitable type of training may be used, e.g., stochastic, gradient boosted, random seeded, recursive, epoch or batch-based, etc.

In the field of pathology, a pathologist may access digital medical images through a digital workflow. With digital workflows, the pathologist may have access to a digital worklist or laboratory information system that notes the status of different cases, which ones are assigned to them, and which are pending more information, etc. This may still require input from the pathologist to filter for certain cases. For example, the pathologist may filter based on pathologist-specific behavior or experience (e.g., the pathologist may want to view excisions first because those are going to take the pathologist more time). As another example, the pathologist may filter based on the site (e.g., biopsies should always be pushed to top of the worklist given the stringent turnaround time).

Pathologists may be under pressure to review more specimens within shorter turnaround times. Pathologists may save significant time using techniques discussed herein, since pathologists may not need to spend seconds navigating back to a worklist, finding a case, and opening the case. In addition, techniques disclosed herein may ensure that cases are provided to pathologists in such a way that efficiency is maximized, fatigue is reduced, and pathologist and administrator preferences are taken into consideration.

With techniques discussed herein, the pathologist might not need to manually curate or customize the worklist, or revisit the worklist each time before going to the next case. After completing the review and producing a report or initial assessment of the case, the pathologist may be automatically be taken to the next case for review.

Pathology departments and/or laboratories are also under pressure to quickly and efficiently turnaround reports to their clients (e.g., clinicians). A system that can create an optimal case order for review based on pathologist preferences, time of day, clinician expectations, specimen type, diagnosis, etc., that will enable shorter turnaround times, may be advantageous to labs and their clients.

FIG. 1A illustrates a block diagram of a system and network for processing images to determine an optimal case order, according to an exemplary technique of the present disclosure.

Specifically, FIG. 1A illustrates an electronic network 120 that may be connected to servers at hospitals, laboratories, and/or doctors' offices, etc. For example, physician servers 121, hospital servers 122, clinical trial servers 123, research lab servers 124, and/or laboratory information systems 125, etc., may each be connected to an electronic network 120, such as the Internet, through one or more computers, servers, and/or handheld mobile devices. According to an exemplary embodiment of the present disclosure, the electronic network 120 may also be connected to server systems 110, which may include processing devices 111. One or more of the processing devices 111 may be configured to implement a tissue viewing platform 100, which includes a slide analysis tool 101 for determining specimen property or image property information pertaining to digital pathology image(s), and using machine learning to classify a specimen, according to an exemplary technique described herein. The tissue viewing platform 100 may also include a case order optimization tool 141 for determining an order in which to present cases to one or more users (e.g., one or more pathologists) to optimize one or more variables given one or more constraints, according to an exemplary technique described herein. In other examples, the case order optimization tool 141 may be operated separately from (e.g., by a different platform than) the tissue viewing platform 100.

The physician servers 121, hospital servers 122, clinical trial servers 123, research lab servers 124, and/or laboratory information systems 125 may create or otherwise obtain images of one or more patients' cytology specimen(s), histopathology specimen(s), slide(s) of the cytology specimen(s), digitized images of the slide(s) of the histopathology specimen(s), or any combination thereof. The physician servers 121, hospital servers 122, clinical trial servers 123, research lab servers 124, and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124, and/or laboratory information systems 125 may transmit digitized slide images and/or patient-specific information to server systems 110 over the electronic network 120. Server systems 110 may include one or more storage devices 109 for storing images and data received from at least one of the physician servers 121, hospital servers 122, clinical trial servers 123, research lab servers 124, and/or laboratory information systems 125. Server systems 110 may also include processing devices 111 for processing images and data stored in the one or more storage devices 109. Server systems 110 may further include one or more machine learning tool(s) or capabilities. For example, the processing devices 111 may include a machine learning tool for the tissue viewing platform 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124, and/or laboratory information systems 125 refer to systems used by pathologists for reviewing the images of the slides. In hospital settings, tissue type information may be stored in one of the laboratory information systems 125.

Figure 1B:
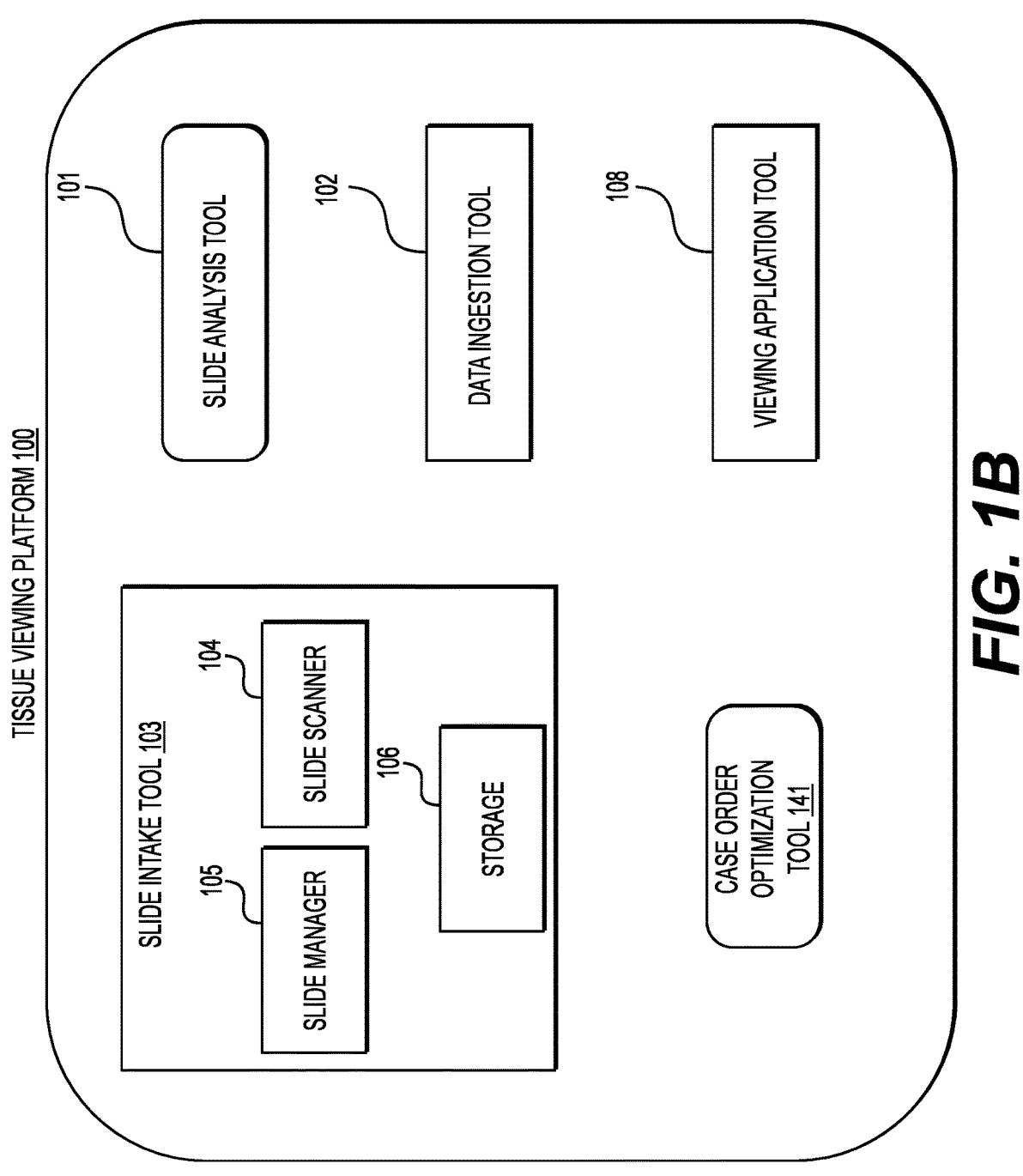
FIG. 1B illustrates an exemplary block diagram of a tissue viewing platform according to techniques presented herein.

FIG. 1B illustrates an exemplary block diagram of the tissue viewing platform 100. For example, the tissue viewing platform 100 may include the slide analysis tool 101, the case order optimization tool 141, a data ingestion tool 102, a slide intake tool 103, a slide scanner 104, a slide manager 105, a storage 106, and a viewing application tool 108.

The slide analysis tool 101, as described in greater detail below, refers to a process and system for processing digital pathology slides (e.g., digitized images of slide-mounted histology or cytology specimens), and using machine learning to analyze a given slide, according to an exemplary embodiment.

The case order optimization tool 141, as described in greater detail below, refers to a process and system for processing digital pathology slides (e.g., digitalized images of a slide-mounted history or cytology specimens), and using machine learning or a rules based system for determining an order in which to present cases to one or more users (e.g., one or more pathologists) to optimize one or more variables given one or more constraints.

The data ingestion tool 102 refers to a process and system for facilitating a transfer of the digital pathology images to the various tools, modules, components, and devices that are used for classifying and processing the digital pathology images, according to an exemplary embodiment.

The slide intake tool 103 refers to a process and system for scanning pathology slides and converting them into a digital form, according to an exemplary embodiment. The slides may be scanned with the slide scanner 104, and the slide manager 105 may process the images on the slides into digitized pathology images and store the digitized images in storage 106.

The viewing application tool 108 refers to a process and system for providing a user (e.g., a pathologist) with specimen property or image property information pertaining to digital pathology image(s), according to an exemplary embodiment. The information may be provided through various output interfaces (e.g., a screen, a monitor, a storage device, and/or a web browser, etc.).

The slide analysis tool 101, and one or more of its components, may transmit and/or receive digitized slide images and/or patient information to server systems 110, physician servers 121, hospital servers 122, clinical trial servers 123, research lab servers 124, and/or laboratory information systems 125 over an electronic network 120. Further, server systems 110 may include one or more storage devices 109 for storing images and data received from at least one of the slide analysis tool 101, the data ingestion tool 102, the slide intake tool 103, the slide scanner 104, the slide manager 105, and the viewing application tool 108. Server systems 110 may also include the processing devices 111 for processing images and data stored in the storage devices 109. Server systems 110 may further include one or more machine learning tool(s) or capabilities, e.g., due to the processing devices 111. Alternatively or in addition, the present disclosure (or portions of the system and methods of the present disclosure) may be performed on a local processing device (e.g., a laptop).

Any of the above devices, tools and modules may be located on a device that may be connected to an electronic network 120, such as the Internet or a cloud service provider, through one or more computers, servers, and/or handheld mobile devices.

Figure 1C:
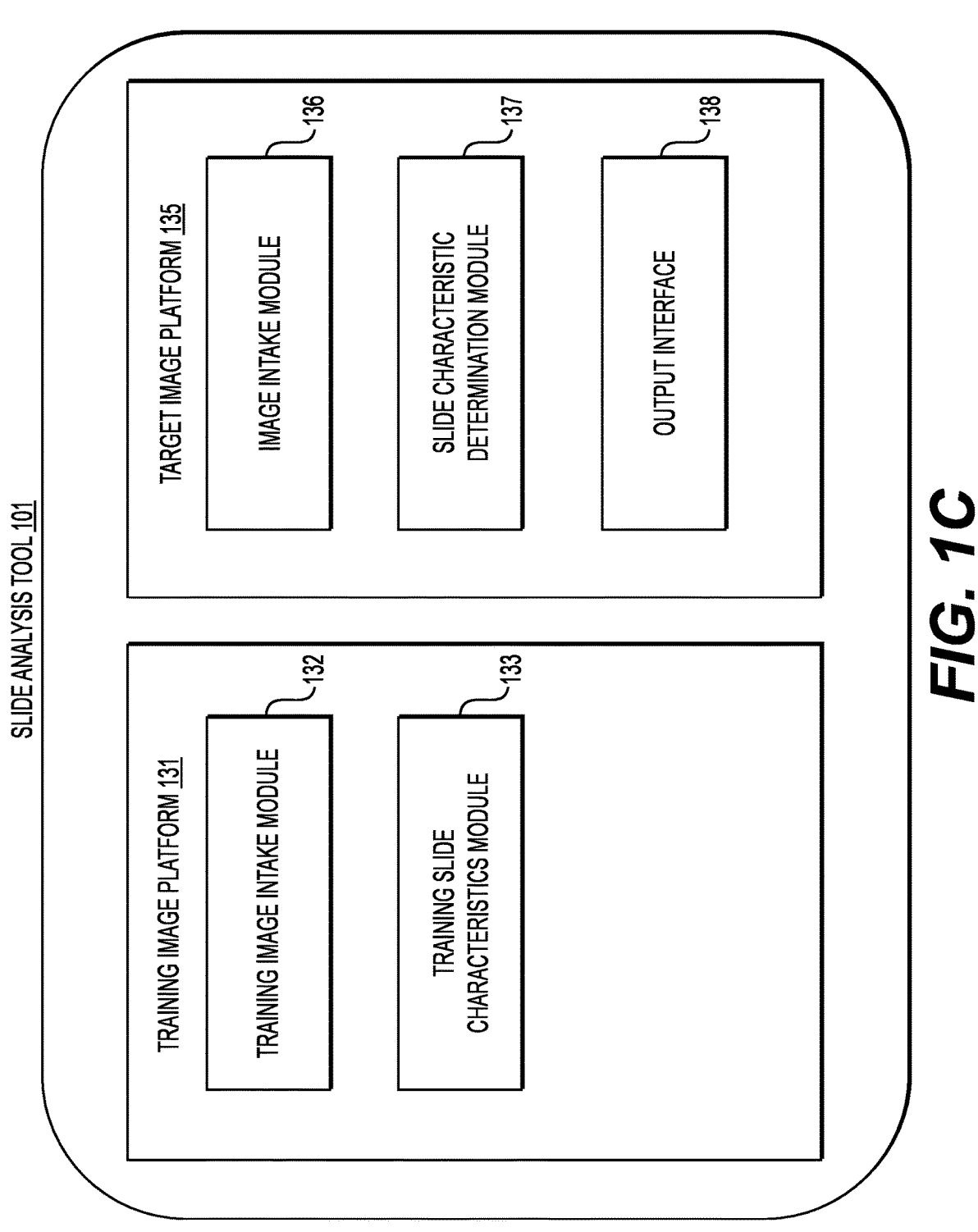
FIG. 1C illustrates an exemplary block diagram of a slide analysis tool, according to techniques presented herein.

FIG. 1C illustrates an exemplary block diagram of the slide analysis tool 101, according to an exemplary embodiment of the present disclosure. The slide analysis tool 101 may include a training image platform 131 and/or a target image platform 135.

The training image platform 131, according to one embodiment, may create or receive training images that are used to train a machine learning system to effectively analyze and classify digital pathology images. For example, the training images may be received from any one or any combination of the server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, Hematoxylin alone, IHC, molecular pathology, etc.; and/or (b) digitized image samples from a 3D imaging device, such as micro-CT.

The training image intake module 132 may create or receive a dataset comprising one or more training images corresponding to either or both of images of a human tissue and images that are graphically rendered. For example, the training images may be received from any one or any combination of the server systems 110, physician servers 121, and/or laboratory information systems 125. This dataset may be kept on a digital storage device. In some examples, the dataset may be comprised of a plurality of data subsets, where each data subset corresponds to a training case from a plurality of training cases and includes one or more training images from the training case. The training slide characteristic module 133 may include one or more computing devices capable of, e.g., determining whether the training images have a sufficient level-of-quality for training a machine learning model. The training slide characteristic module 133 may further include one or more computing devices capable of, e.g., identifying whether a set of individual cells belong to a cell of interest or a background of a digitized image.

The target image platform 135 may include one or more computing devices capable of, receiving a target dataset and applying a machine learning model to the received target dataset to determine one or more characteristics of the target dataset. In some examples, the target dataset may include one or more target images included in a case. Characteristics of the target dataset may include, but are not limited to, case complexity, case type, number of areas of interest per slide, amount of tissue per slide, and/or an image quality. For example, the target dataset may be received from the server systems 110, the physician servers 121, the hospital servers 122, the clinical trial servers 123, the research lab servers 124, and/or the laboratory information systems 125. The target image intake module 136 may include one or more computing devices capable of, e.g., receiving a target dataset. Slide characteristic module determination 137 may include one or more computing devices capable of, e.g., applying a machine learning model to the target dataset to determine case complexity, case type, number of areas of interest, amount of tissue per slide and/or image quality. The Slide characteristic module determination 137 may also be responsible for identifying the amount of image that one or more pathologist may need to review in connection with the inputted case. For instance, the Slide characteristic module determination 137 may identify all prior cases that a patient has that may need to be reviewed/revisited.

The output interface 138 may include one or more computing devices capable of, e.g., outputting information about the target dataset and the determined relationship (e.g., to a screen, monitor, storage device, web browser, etc.). In some examples, the output interface 138 may provide the case complexity, case type, number of areas of interest, amount of tissue per slide, and/or an image quality to the case order optimization tool 141, e.g., to be used as an input for one or more other processes.

Figure 2:
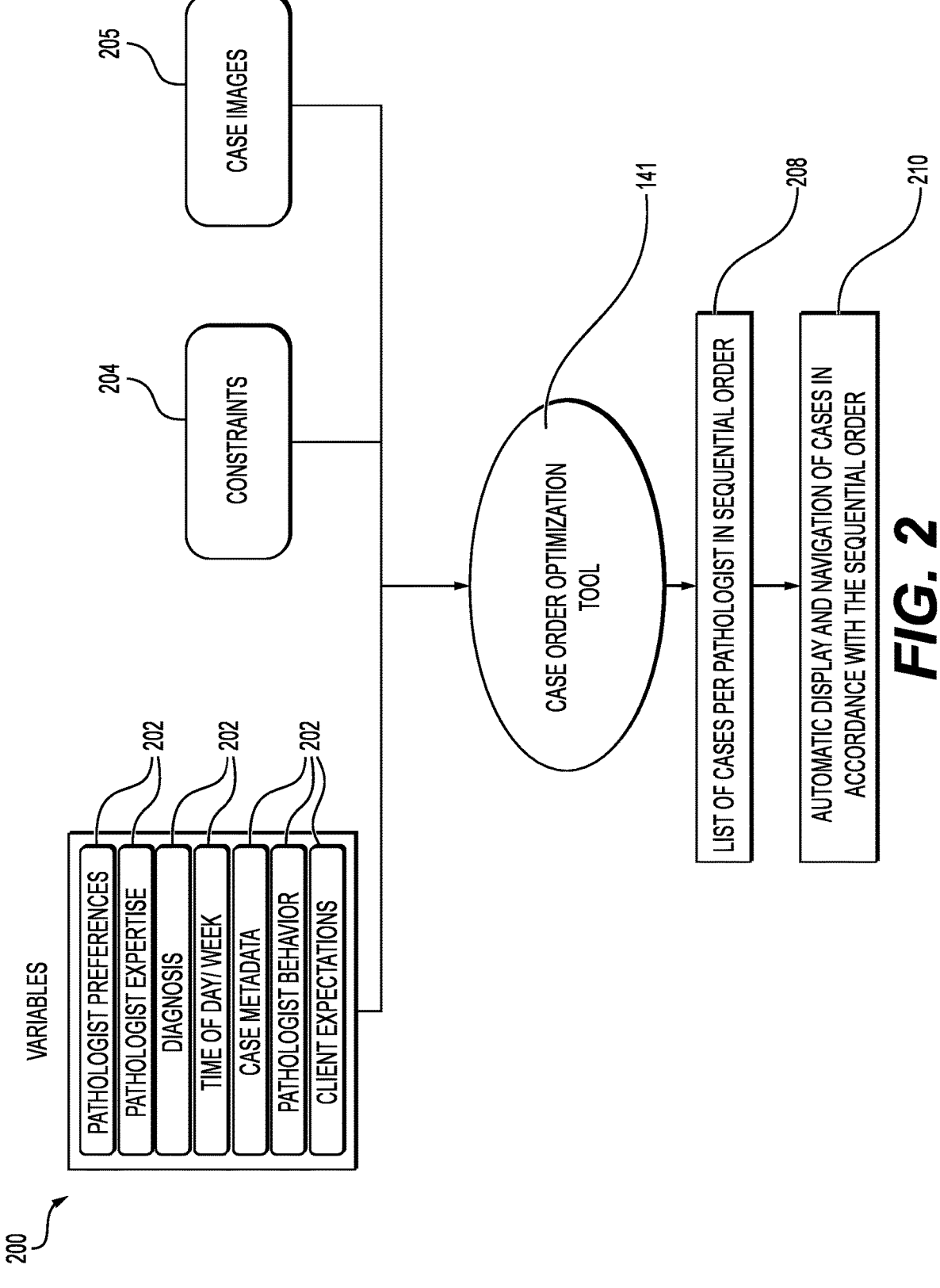
FIG. 2 is a flow diagram illustrating an exemplary process for using a trained system to determine an optimized case order, according to techniques presented herein.

FIG. 2 is a flow diagram 200 illustrating an exemplary process for using a trained system to determine an optimized case order. The trained system may be implemented by the case order optimization tool 141 of the tissue viewing platform 100. The case order optimization tool 141 may utilize the trained system to determine a sequential order for presenting each case of a plurality of cases to be reviewed that optimizes one or more variables 202 within the boundaries of one or more constraints 204. Each case may include one or more case images 205, where the determined order may be further based on the case images 205 and/or output from an analysis thereof (e.g., output from the slide analysis tool 101).

For example, the case order optimization tool 141 may receive one or more variables 202. Variables 202 may include important factors to consider to inform case order. Variables 202 may vary by pathologist, by site, by institution, etc. The variables 202 may include, but are not limited to, pathologist preferences, a number of cases to be reviewed per day, pathologist expertise, quality of diagnosis, time of day, day of week, pathologist behavior, client expectations, and/or laboratory considerations, each described in turn below. The variables 202 may be input as numbers (e.g., time of day) or text. For variables 202 that are input as text, a rule-based text extraction system may be used to extract the information from one or more datasets received. The case order optimization tool 141 may allow for a user (e.g., pathologist, department manager, administrator) to enter any of the variables 202 discussed within this application.

Pathologist preference may refer to a type of case that a pathologist prefers and/or does not prefer to analyze. For example, a pathologist may not prefer to review prostate cancer cases. In some aspects, the case order optimization tool 141 may display a list of case types, and the user can select one or more of the case types that they prefer to review and/or one or more of the case types that they prefer not to review from the list. Further, the user may be able to rank case types by highest preference and lowest preference. A number of cases to be reviewed per day may refer to a desired amount of cases that a particular pathologist may review in a day or set period of time, which may be input by a system administer or by the particular pathologist.

Pathologist expertise may refer to a level of expertise that a pathologist has for one or more types of cases. The case order optimization tool 141 may allow for a pathologist to select from all available case types and to choose which cases the pathologist has expertise in. Further, the pathologist may be able to provide a score (e.g., a number from 1 to 10) indicating an expertise level for each type of case. Additionally, the case order optimization tool 141 may track or log cases that have been reviewed by a particular pathologist to update the expertise of particular individuals. Quality of diagnosis may refer to the rate at which a diagnosis for a particular type of case is overturned and/or contradicted by a second review pathologist. The quality of diagnosis variable may be an overall rating for all diagnoses performed and/or a rating per case type.

Time may refer to what time of day it is (e.g., morning versus afternoon) and/or what day of week it is (e.g., Monday versus Friday). The case order optimization tool 141 may receive and/or generate temporal information related to how a pathologist's quality and/or speed of review is affected depending on what time of day it is and/or what day of the week it is. Case metadata may refer to data associated with a patient's case, such as a case type, a number of digital slides, an amount of tissue on each of the digital slides, a number of areas of interest in each digital slide, and/or a number of previous cases associated with a same patient. In some examples, a portion of the case metadata may be received from the storage devices 109, clinical trial server 123, physician servers 121, laboratory information system 125, research lab servers 124, and/or hospital servers 122. Additionally or alternatively, a portion of the case metadata may be received as output of the slide analysis tool 101.

Pathologist behavior may refer to data related to how a pathologist interacts with the viewing application tool 108, e.g., to review cases. The data may include general usage of the viewing application tool 108, including fatigue and/or user burnout, relative speed of review based on a total time reviewing a slide of a particular type, a total time reviewing a case of a particular type, etc. obtained based on input speed (e.g., mouse, keyboard, touch, eye tracking, etc.). Client expectations may refer to a turnaround time for the pathologist's report and/or initial assessment from the time the cases are forwarded to the department or lab for review. In some examples, the turnaround time may be a standard time period across cases. However, certain individual cases or case types may be of higher importance and/or of a more time sensitive manner. Thus, these individual cases or case types may be digitally marked to indicate a higher priority and thus a quicker turnaround time expected by the client. In one example, this digital marking may be equivalent to certain cases that are marked as "Stat" during manual review. In other examples, a case may be automatically identified as higher priority based on case type, e.g., regardless of whether the case is digitally marked. For example, a biopsy may be automatically identified as higher priority given the turnaround time expected is typically more stringent. Laboratory considerations may refer to considerations around a particular case, such as diagnosis, number of pathologists available that day, or further testing requirements. For example, if a case is likely to require additional testing based on a diagnosis, which could be informed by AI before the pathologist looks at the case, the need for further testing may take priority over some other cases to be added to the pathologist's queue.

The case order optimization tool 141 may further receive one or more constraints 204. Constraints 204 may include goals or key performance indicators (KPIs) that may need to be met by a pathologist. Example constraints may include, but are not limited to, pathologists available for review, pathologist qualifications, case deadlines, time left in a shift or in the day, and/or department goals. Pathologists available for review may refer to a list of all potential pathologists and/or at least a number of all potential pathologists available during a particular time or particular day, who may be capable of performing review of cases generally. Pathologist qualifications may include particular types of cases a pathologist (e.g., from the available pathologists) is trained and/or has the expertise to handle. Case deadline may refer to a specific day and/or time that a case needs to be analyzed by. In one example, the case deadline may be extracted as metadata that is included with the particular cases. The case deadline may also be auto determined based on the standard turnaround time for a particular case type. The deadline may be adjusted to account for a case that is marked as higher priority (e.g., the case must be analyzed within 24 hours of the system receiving the case for a higher priority case). Additionally, the case deadline can be input and/or modified externally by a pathologist as a case/case load is inputted.

Time left in a shift or day may refer to the period of time that one or more of the available and/or qualified pathologists has left in the day to analyze cases. For instance, shift schedules that include a time of day that each available and/or qualified pathologist starts and stops working may be received, and the case order optimization tool 141 may track the amount of time in the day left until the stop time. Further, the case order optimization tool 141 may subtract breaks, such as set lunch break time periods and/or other mandated breaks, from the time left in the shift to accurately reflect how much working time each pathologist has left in the shift. Department goals may refer to specific types of cases or cases for particular patients having higher priority to be analyzed within a specific period of time. Department goals may also refer to a number of total cases that the department may wish to analyze over a period of time, such as total cases for an individual pathologist and for a laboratory as a whole. A department goal may also refer to an average accuracy rate that the laboratory may try to achieve across all pathologists within the laboratory.

While variables 202 have been discussed herein as optional factors to be optimized, and constraints 204 are discussed herein as requirements to be met that limit or define the boundaries of the case assignments and orderings, the specific examples or types of constraints 204 discussed herein may, in some instances, be designated as a variable 202, and vice versa, by the users and/or administrators. For example, a department goal may be a constraint 204 that must be met, or it may be designated as a variable 202 to be optimized relative to other variables 202. For example, in some instances the number of pathologists available to review cases may be a constraint 204. In other instances, it may be possible to call in other pathologists for assistance, and thus the number of pathologists may be selected or indicated as a variable 202 to be optimized.

The case order optimization tool 141 may further receive case images 205 for a plurality of cases to be analyzed. The case images 205 may include digitized pathology images. As stated above, examples of digital pathology images may include (a) digitized slides stained with a variety of stains, such as (but not limited to) H&E, Hematoxylin alone, IHC, molecular pathology, etc.; and/or (b) digitized image samples from a 3D imaging device, such as micro-CT. The case images 205 may also be referred to as whole slide images (WSIs). The case order optimization tool 141 may receive one or more case images 205 per case. Accordingly, the case order optimization tool 141 may receive a plurality of sets of one or more WSIs, each set corresponding to each case of the plurality of cases. In some examples, other case-related data, such as patient data, may be received in addition to the case images 205. The case-related data, including at least the case images 205, may be imported from the storage devices 109, clinical trial server 123, physician servers 121, laboratory information system 125, research lab servers 124, hospital servers 122, or from an external network. Further, these case images 205 may be imported through external storage devices such as a flash drive. The case order optimization tool 141 may be capable of constantly receiving new case images 205 corresponding to new cases and updating the case order to incorporate the new cases as the new case images 205 are received.

In some examples, the case order optimization tool 141 may also receive an output from an analysis or evaluation of the case images 205 performed, e.g., by the slide analysis tool 101. These analysis and/or evaluation outputs may optionally be received and/or implemented as variables 202. Exemplary analysis or evaluation outputs may include an AI evaluation of slides that may determine the case complexity vs. a time required to evaluate a particular case, the case type, the number of areas of interest, the amount of tissue per slide, the number of slides in the case, and/or the number of prior cases that a patient has that the pathologist would also have to review. The case complexity may be determined part based on the number of regions of interest (e.g., salient regions). The salient regions may be determined in accordance with techniques discussed in U.S. patent application Ser. No. 17/313,617, filed May 6, 2021, which is herein incorporated by reference in its entirety.

The case order optimization tool 141 may utilize a trained system to determine a sequential order for presenting each case of the plurality of cases to be reviewed while optimizing one or more of the variables 202 within the boundaries of the constraints 204. For example, the case order optimization tool 141 may provide one or more variables 202 and constraints 204 along with the case images 205 (and optionally the corresponding case image analysis or evaluation outputs from the slide analysis tool 101) as input to the trained system. The trained system may determine and output a sequential order for presenting each case of a plurality of cases to be reviewed. For example, the cases may be assigned among one or more pathologists, and for each load of cases assigned to a pathologist, a review order for the cases may be determined.

When performing the case order determination, the trained system may optimize one or more of the variables 202 received as input based on the one or more constraints 204 received as input. In some examples, the variables 202 may be automatically optimized. In other examples, the variables to be optimized may be selected by a user (e.g., a pathologist, department manager, administrator, etc.). The user may also select and/or modify the constraints 204 for the determination. As one example, the trained system may generate a plurality of possible case assignments and case orderings per assignment, all within the constraints 204. The trained system may determine a score for each of the plurality of possible assignments and case orderings per assignment. The score may be based upon a degree or level to which the variables 202 to be optimized are met. The assignment of cases and ordering of cases within that assignment having the highest score may be output by the trained system.

When multiple variables 202 (e.g., more than one variable) are to be optimized, each optimized variable 202 of the multiple variables 202 may be assigned a score, and the trained system may output the assignments and ordering of cases therein that maximizes the overall score. For example, when one set of assignments and case orderings has a high score for a first variable but a low score for a second variable, and a second set of assignments and case orderings has a low score for the first variable but a high score for the second variable, the trained system may select to output whichever set has the highest overall score. The trained system may further consider an indicated priority of the first and second variables, if any, when selecting. The indicated priority may also be considered in view of the constraints 204. For example, if a pathologist preference is not to review prostate cancer (e.g., a first variable), but there are many prostate cancer cases and a department goal of completing them that day (e.g., a constraint), the trained system may nonetheless assign some prostate cancer cases to the pathologist to ensure that the constraint is met (e.g., resultantly not optimizing the first variable). In such an instance, the trained system may instead optimize a second variable, such as the best time of day for the pathologist to review or a type of prostate cancer case to assign to the pathologist. The trained system may conform to any number of constraints 204, for example, if a particular case is an emergency case, an immediate review of the case may be included as a constraint and the case may prioritized accordingly.

In some examples, the trained system may be a trained machine learning (ML) system. Exemplary types of ML systems that may be trained and implemented for the optimized case order determination may include, but are not limited to, reactive machines and limited memory machines. In some examples, the ML system may include a neural network for objective function approximation. Training and implementation of the ML system are described in detail below. Additionally or alternatively, the trained system may be a rule-based system (e.g., apply rule-based logic) to determine the optimized case order. In some examples, whether the trained system is ML-based or rule-based may be dependent on the optimization.

Once the optimized case order has been determined, the trained system may output one or more lists of cases 208 based on the determination. For example, each list of cases 208 may be specific to (e.g., assigned to) a particular pathologist within a department or lab to review. The sequential order of the cases 208 within the list may represent the optimized case order in which the cases 208 are to be reviewed by the pathologist. In some examples, the list of cases 208 may identify the cases based on a case number or other identifier to allow for automatic look-up and presentation of one or more case images 205 for each case, as discussed in more detail below. In other examples, the list of cases 208 may include the one or more case images 205 for each case. The trained system may output an updated list of cases 208 as additional cases and the respective case images 205 thereof are received. In some examples, the update may be performed each time a new case is received. In other examples, the update may be performed at periodic time intervals. Additionally, the trained system may output an updated list of cases 208 as one or more variables 202 and/or constraints 204 are modified. For instance, if a previously available pathologist for a particular lab was now unable to work on a given, the list of cases 208 may then be updated to e.g., reassign cases and update case orderings for other available pathologists for the particular lab.

In some examples, at process 210 the case images 205 of each case may be automatically provided for display to the user in accordance with the sequential order of cases provided in the list of cases 208. In some examples, the cases images 205 may be displayed via a user interface of the viewing application tool 108. For example, case images 205 for a next case in the list of cases 208 may automatically be displayed to the user interface once a review or analysis of case images 205 for a current case (e.g., preceding the next case in the list) is completed. In some examples, the pathologist may select a single user interface option such as a "next case" button or control element (e.g., via touch or click of mouse), select a hotkey (e.g., on a keyboard), and/or or provide some other gesture or indication to indicate that the review or analysis of case images 205 for the current case has been completed and the case images 205 for the next case in the list may be displayed. In other examples, no direct inputs may be required from the user, and the viewing application tool 108 may automatically detect that the review or analysis of the current case has been completed (e.g., may automatically detect that an event associated with case review completion has occurred). For example, based on the user having viewed all case images 205 of the current case, and/or having entered a report or an initial assessment, a determination may be made that the current case review has been completed. While user interfaces of the viewing application tool 108 are described above as displaying the cases in sequential order for pathologist review, user interfaces of any systems used by pathologist to review and/or analyze cases or WSIs may be configured to include the same functionalities, including other user interfaces of the tissue viewing platform 100 (e.g., separate from the viewing application tool 108).

In some examples, when one or more case images 205 from a case are displayed to a user, the user may receive the particular images from within the case in a previously specified order. As one non-limiting example, when a case is displayed to a user, the images for the case may be ordered in accordance with prioritization techniques discussed in U.S. patent application Ser. No. 16/887,855, filed May 29, 2020, which is herein incorporated by reference in its entirety.

In further examples, and as previously discussed a separate machine learning system (e.g., of the slide analysis tool 101) may be utilized to analyze the images within the cases prior to displaying the images to one or more users. For example, the separate machine learning system may identify areas of interest for the one or more users, and the areas of interest may be provided as input to the case order optimization tool 141 and/or to other processes. The area of interest may be determined in accordance with techniques discussed in U.S. patent application Ser. No. 17/014,532, filed Sep. 8, 2020, which is herein incorporated by reference in its entirety. Further, the images themselves may be displayed to a user in accordance with techniques discussed in U.S. patent application Ser. No. 17/014,532.

The case order optimization tool 141 may be operated in a plurality of different contexts, including clinical, research, and educational contexts. In some examples, the training and implementation of the trained system for determining the optimized case order may be dependent on the context. The training and implementation of the trained system is described in turn below for each of the clinical, research, and educational contexts.

Figure 3A:
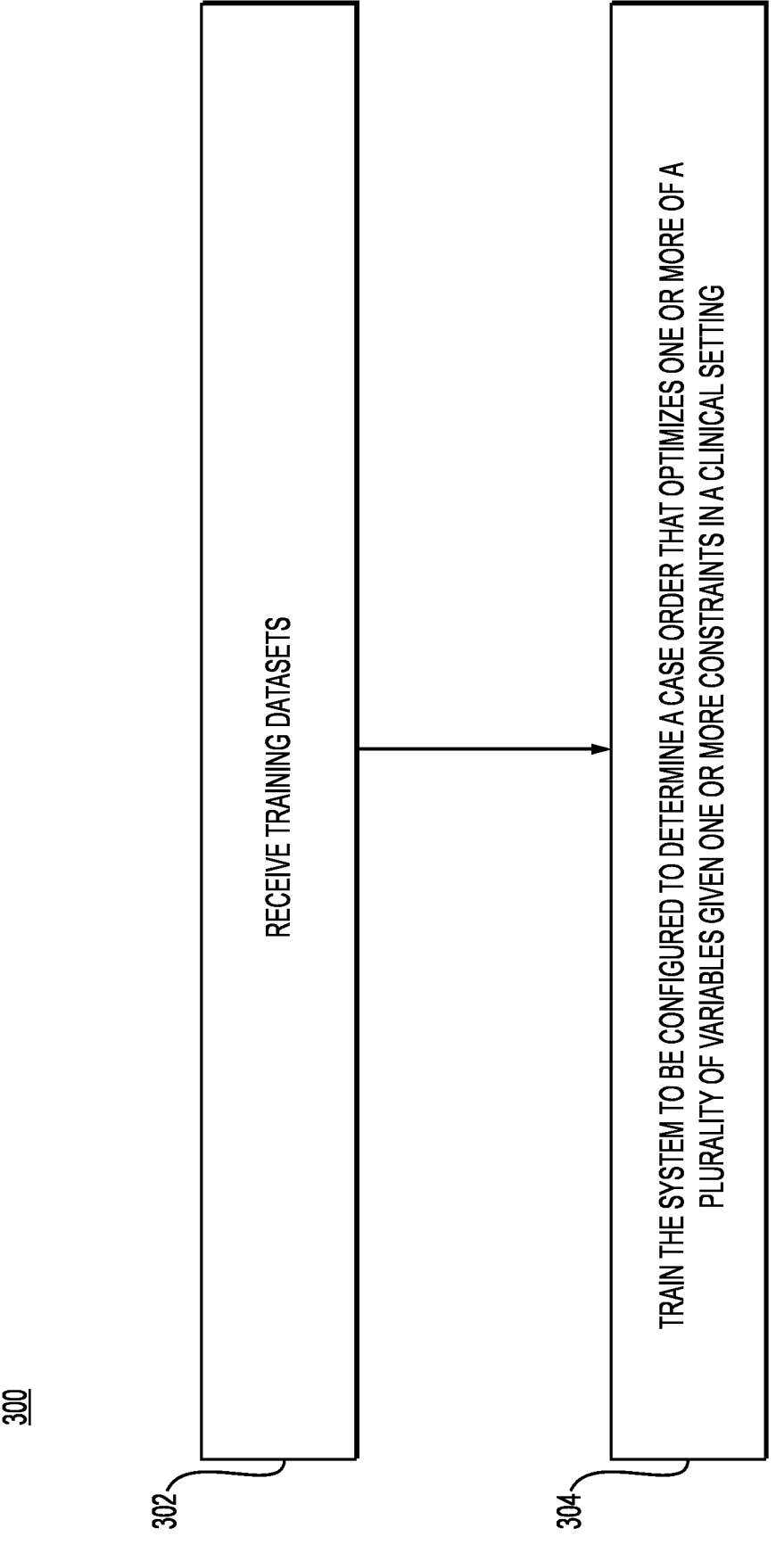
FIG. 3A is a flowchart of an example method for training a system to determine an optimized case order in a clinical context, according to techniques presented herein.

FIG. 3A is a flowchart of an example method 300 for training a system to determine an optimized case order in a clinical context, according to techniques presented herein. The method 300 of FIG. 3A depicts steps that may be performed by, for example, case order optimization tool 141. Alternatively, the method 300 may be performed by an external system, where the trained system may be provided to the case order optimization tool 141 for implementation.

At step 302, a plurality of training datasets may be received. Training datasets may include variables 202, constraints 204, and/or cases images 205. Additional training datasets may include data associated with general usage of the application, where the usage data may also include tracked data related to fatigue of pathologists, and/or user burnout (e.g., variables 202). For example, a relative review speed (e.g., indicated by mouse speed, keystroke speed, eye tracking speed, total time reviewing a slide of a particular type, total time reviewing a case of a particular type, etc.) of individual pathologists may be determined based upon type of case, experience level for that type of case, time of day, time since the pathologist's last break, level of experience, etc. Utilizing this type of data for training enables the trained system to be able to, e.g., predict a fatigue level of pathologists, generally or individually, moment-by-moment, or at any point throughout the day, which may be factored into the optimization.

The received datasets may also include data from the viewing application tool 108, e.g., that tracks how pathologists are navigating pathology slides (e.g., variables 202). In one example, data may include measurements of how long a pathologist examines each slide. Data may further include tracking of whether the user is using shortcuts and/or hotkeys to perform actions or tasks associated with the tissue viewing platform 100, and/or a time period the user is staring at a pathology slide. As more data is captured for a pathologist, the system may be re-trained to enable greater specificity to the individual pathologists to improve an accuracy of case assignments and case ordering. If no data has been captured for the pathologist (e.g., the pathologist is new to the laboratory or site), a generically trained system may be applied. At this point, the system may then start receiving data of the new pathologist and re-training. For example, this data may then be utilized as variable 202 information to update the case assignment and order output for a particular user.

The received datasets (e.g., variables 202) may further include survey data and historical data. The survey data may include data about satisfaction, pathologist demographics, experience levels, and any other received data from patholo- gist preferences and dislikes. The historical data may include data about a pathologist's past shifts (e.g., days and hours worked), years of experience, experience level generally, experience with particular types of slides, general pathologist preferences, and initial quality assessment of diagnosis (e.g., whether an initial diagnosis was contradicted by a second review). The historical data may also include rates of sample types generally (e.g., an average number of samples and/or samples of given types received per day) and rates of sample types at particular sites (e.g., as certain laboratories dependent on location near specialty hospitals or clinical centers may receive more cases generally and/or more cases of a specific type).

In addition, the training datasets may include information associated with any of the types of variables 202 and/or constraints 204 previously discussed with reference to FIG. 2.

Optionally, the slide analysis tool 101, for example, may utilize one or more machine learning systems to evaluate slides to, e.g., determine case complexity versus time spent evaluating, case type, areas of interest and number thereof, amount of tissue per slide, number of slides in the case, and/or number of prior cases associated with a same patient that the pathologist would also have to review. In some examples, the slide analysis tool 101 may determine case complexity at least in part by determining a number of regions of interest (e.g., determining salient regions).

At step 304, the system may be trained using one or more of the datasets. For example, the system may use the AI-evaluated images and/or the received datasets to train the system to be configured to determine a case order that optimizes one or more of a plurality of variables given one or more constraints in a clinical setting. In the clinical setting or context, the one or more variables optimized may be associated with pathologist efficiency. For example, the variables optimized may include a number of cases completed per day, initial assessment quality/quality of diagnosis (e.g., to achieve a high percentage of initially correct diag- nosis), pathologist retention, and/or number of cases per day while minimizing pathologist fatigue. As previously dis- cussed in detail with reference to FIG. 2, the trained system may be a trained ML system or may apply rule-based logic depending on the optimization.

FIG. 3B is a flowchart illustrating an example method 350 for using a trained system to determine case order optimi- zation in a clinical context, according to one or more exemplary embodiments herein. The exemplary method 350 (e.g., steps 352-358) of FIG. 3B depicts steps that may be performed by, for example, the case order optimization tool 141. These steps may be performed automatically or in response to a request from a user (e.g., a pathologist, a department or laboratory manager, an administrator, etc.). Alternatively, the method 350 may be performed by any computer process system capable of receiving image inputs such as device 700 and capable of storing and executing the trained system described in FIG. 3A.

At step 352, the trained system may receive a plurality of electronic medical images of pathology slides associated with pathology cases. The received electronic medical images of pathology slides may correspond to and be the same type of slides as described for case images 205 from FIG. 2. At step 354, the trained system may further receive any constraint data 204 and/or variable data 202. The constraint data 204 may be any of the constraint data 204 described in FIG. 2. The variable data 202 may be any of the variable data 202 described in FIG. 2.

At step 356, the trained system may determine one or more sequential orders of the pathology cases for review by one or more users. In some examples, a subset of the cases may be assigned to each available user (e.g., pathologist) at a site, and a sequential order for review of cases within each subset may be determined. Optionally, the sequential order may also define an order for the images of each case. The sequential order determined may optimize one or more variables from the received variable data given one or more constraints from the received constraint data. In some examples, the trained system may receive a user-selected variable and/or variables to optimize. In other examples, the trained system may automatically select the variables to be optimized.

At step 358, the trained system may output the determined sequential orders of the pathology cases for review by one or more pathologists (e.g., within a list). In some examples, and as described in greater detail with reference to process 210 of FIG. 2, the electronic medical images for each case may be automatically displayed (e.g., auto-navigated to) according to the sequential order.

In some examples, incoming electronic medical images of pathology slides for new cases may be provided to the trained system as they are received by case order optimiza- tion tool 141. The trained system may then continuously or at predefined intervals update the optimized order.

In one example, the trained system may optimize the case order for one or more individual pathologists. In another example, the trained system may optimize the case order for a site or group of pathologists rather than the individual pathologists within the site or group. In a further example, the trained system may optimize the case order more gen- erally without considering individual pathologist data or site data.

In some examples, the case order optimization tool 141 may further be capable of generating and causing display of a notification to prompt a break for one or more users as they are reviewing their cases. For example, the tool may provide an alert noting that a certain time is a good time to do research if certain portion(s) of the day should be research (e.g., a constraint 204). Additionally, if the tool notices that the quality of review declines over the course of the day, the tool may prompt breaks to attempt to prevent a user's quality of review from decreasing.

In further examples, the case order optimization tool 141 may monitor, for each user, a quality of diagnoses, a number of cases reviewed per day, how speed of review declines over the day, survey data about satisfaction, and demographics of users. Additionally, the case order optimization tool 141 may automatically map the individual variables 202 and feed them to the trained system for re-training, which may happen at predetermined and/or user-defined intervals. For examples, the case order optimization tool 141 may take user data from the case review session, and feed the data back to the trained system, which may then be used to adjust and/or modify the trained system such that it is more accurate or provides better optimization at the outset when used to determine a case order for a new pathologist and for any particular repeat pathologist. This may include leveraging outputs from machine learning systems (e.g., of the slide analysis tool 101) that have analyzed the slides and giving the right case to the right pathologist. For example, if certain users/types of slides usually get a second opinion/review, the trained system may provide these cases earlier in the optimized case order list. The system may additionally take into account which pathologists/users are available and what levels of expertise they may have. The trained system may further identify which cases will need a second opinion or review.

Figure 4A:
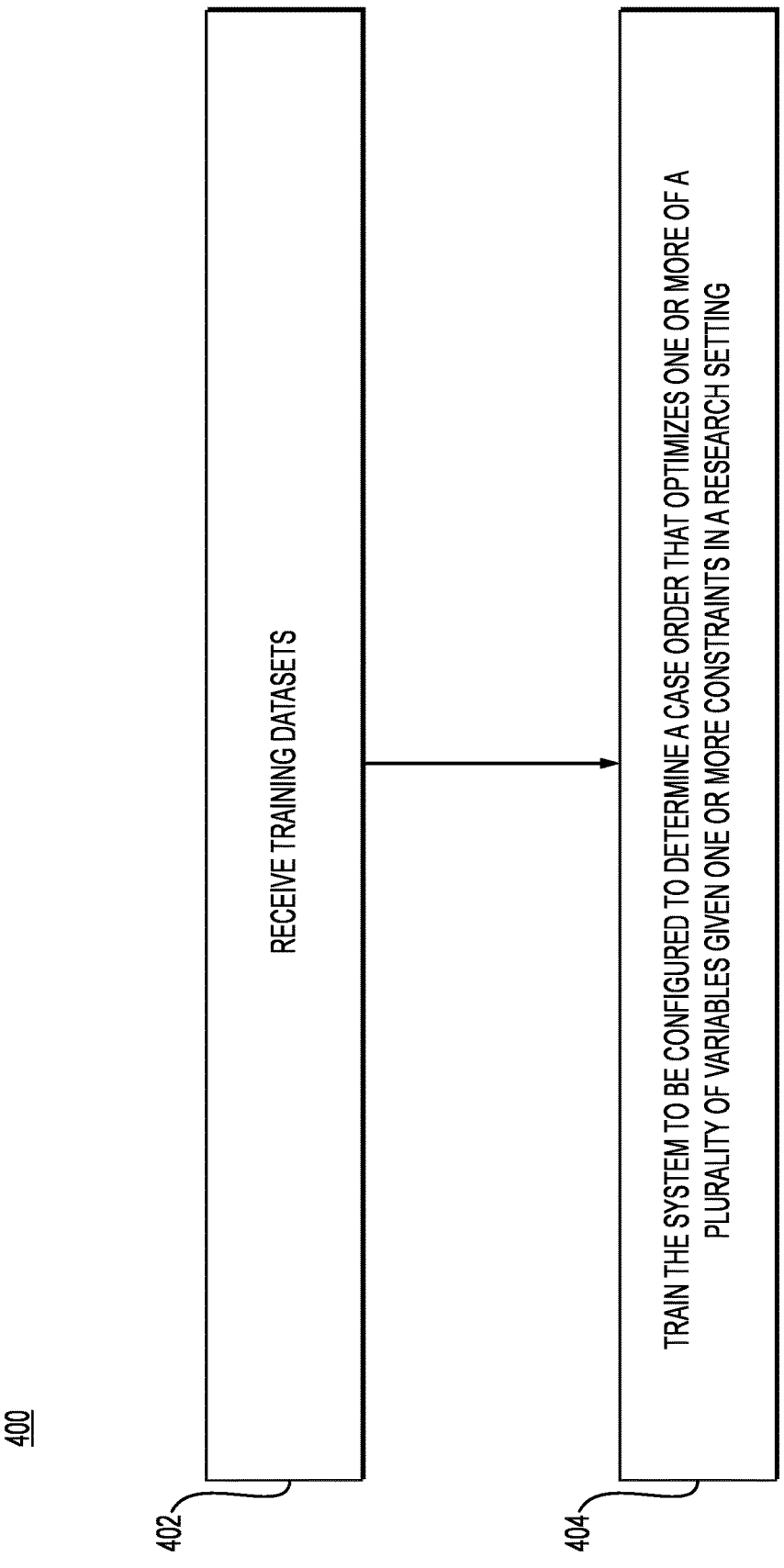
FIG. 4A is a flowchart of an example method for training a system to determine an optimized case order in a research context, according to techniques presented herein.

FIG. 4A is a flowchart of an example method 400 for training a system to determine an optimized case order in a research context, according to techniques presented herein. The method 400 of FIG. 4A depicts steps that may be performed by, for example, the case order optimization tool 141 as described above in FIG. 1C. Alternatively, the method 400 may be performed by an external system, where the trained system may be provided to the case order optimization tool 141 for implementation.

In a research context, including clinical research and clinical trial settings, rendering a diagnosis as part of the case review may not be necessary. For example, while the user may be tasked to identify certain aspects of a pathology slide (e.g., certain characteristics or patterns), the diagnosis associated with these characteristics or patterns may not be critical or already known. As one illustrative example, within a molecular diagnostic lab, the user may review a pathology slide to circle tumors and determine what a machine should scrape rather than diagnose the tumors. Therefore, within the research context, the trained system might not perform case order optimization for quality of diagnosis, but rather for certain performance metrics. For example, case order optimization may prioritize a speed variable more than an accuracy variable.

Generally, the training phase detailed in steps 402-404 of method 400 may incorporate any of the steps or features discussed in method 300 (e.g., the training phase in a clinical context). For example, the trained system, at step 402 may receive datasets that include any of the datasets received at step 302 of method 300 discussed with reference to FIG. 3A

At step 404, the system may be trained using one or more of the datasets. For example, the system may utilize the AI-evaluated images and/or the received datasets to train the system to be configured to determine a case order that optimizes one or more of a plurality of variables given one or more constraints in a research setting. For example, the system may be trained at step 404 similar to step 304, except for the variables optimized may be different. For example, in the clinical research and/or clinical trial setting or context, the one or more variables optimized may be associated with pathologist efficiency or any other optimal variable related to clinical research. For example, the variables optimized may include the number of cases completed, number of salient regions reviewed per predetermined time period, and/or number of slides reviewed in a day. As previously discussed in detail with reference to FIG. 2, the trained system may be a trained ML system or may apply rule-based logic depending on the optimization.

FIG. 4B is a flowchart illustrating an example method 450 for using a trained system to determine case order optimization in a research context, according to one or more exemplary embodiments herein. The exemplary method 450 (e.g., steps 452-458) of FIG. 4B depicts steps that may be performed by, for example, by the case order optimization tool 141. These steps may be performed automatically or in response to a request from a user (e.g., a pathologist, a department or laboratory manager, an administrator, etc.). Alternatively, the method 450 may be performed by any computer process system capable of receiving image inputs such as device 700 and capable of storing and executing the trained system described in FIG. 4A.

Generally, the production phase, described in method 450, may incorporate any of the steps or features of method 350 discussed in FIG. 3B. At step 452, the trained system may receive a plurality of electronic medical images of pathology slides associated with pathology cases. At step 454, the trained system may further receive any variable data 202 and/or any constraint data 204. At step 456, the trained system may determine one or more sequential orders of the pathology cases for review by one or more users in a research setting. In some examples, a subset of the cases may be assigned to each available user (e.g., pathologist) at a site, and a sequential order for review of cases within each subset may be determined. Optionally, the sequential order may also define an order for the images of each case. The sequential orders determined may optimize one or more variables from the received variable data given one or more constraints from the received constraint data. For example, the trained system may be optimized for pathologist performance metrics over quality of diagnosis in the research setting or context. For example, case order optimization may prioritize a speed variable more than an accuracy variable. In some examples, a user may select specifically which variables to optimize for during this step. In other examples, the trained system may automatically select the variables to be optimized.

At step 458, the trained system may output the determined sequential orders of the pathology cases for review by one or more pathologists (e.g., within a list). In some examples, and as described in greater detail with reference to process 210 of FIG. 2, the electronic medical images for each case may be automatically displayed (e.g., auto-navigated to) according to the sequential order.

Figure 5A:
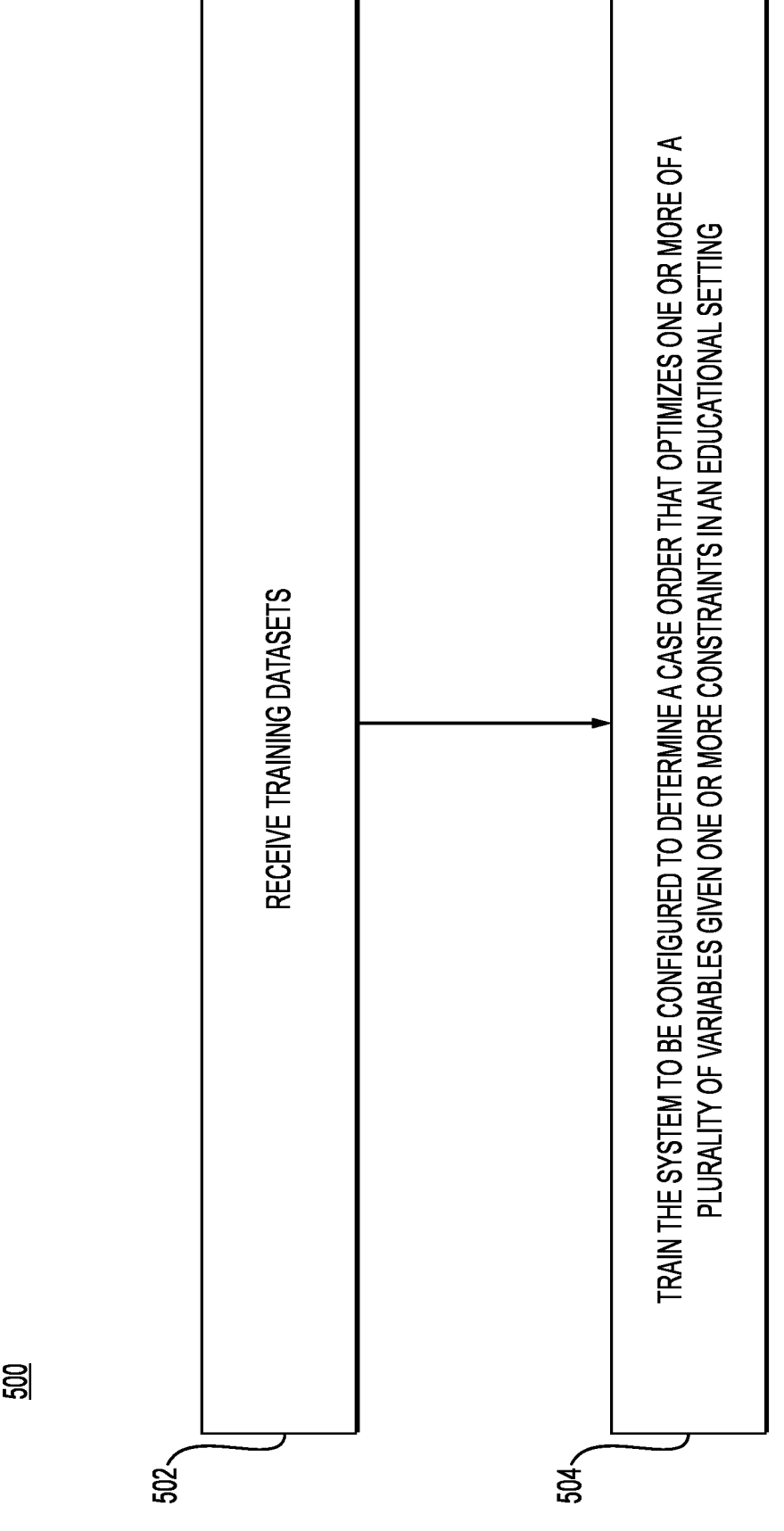
FIG. 5A is a flowchart of an example method for training a system to determine an optimized case order in an educational context, according to techniques presented herein.

FIG. 5A is a flowchart of an example method 500 for training a system to determine an optimized case order in an educational context, according to techniques presented herein. The method 500 of FIG. 5A depicts steps that may be performed by, for example, the case order optimization tool 141 for implementation as described above in FIG. 1C. Alternatively, the method 500 may be performed by an external system, where the trained system may be provided to the case order optimization tool 141 for implementation.

The case order optimization tool 141 may be utilized within an educational context for training and/or testing users (e.g., students training to become pathologists and/or pathologists continuing their training). From an educational perspective, a variation of case types may be necessary for the general understanding or testing of users. Additionally, identification and/or presentation of similar/same case types to individual students based on areas where improvement is needed may also be helpful. Therefore, variables to be optimized for the case order determination within the educational context may be variables associated with pathologist improvement, rather than accuracy or speed. Additionally, diagnoses associated with each case may be known by the case order optimization tool 141.

Further, the case order optimization tool 141 may allow users to choose certain case areas for practice. The case order optimization tool 141 may automatically suggest a break if quality is declining (e.g., if a number of incorrect diagnoses provided by the user within a predefined time period or number of cases is above a threshold). The case order optimization tool 141 may further track a user's progress over time and remember individual user's strength and weaknesses for further use. A user's strength may refer to a particular area or field of pathology for which the user correctly identifies a diagnosis at a rate above a particular threshold value (e.g., 80% or greater of the time diagnosis is correct) or at a rate higher than the user's overall diagnosis rate. A user's weakness may refer to a particular area or field of pathologist for which the user incorrectly identifies a diagnosis at a rate below a particular threshold value (e.g., 50% or less of the time diagnosis is incorrect) or at a rate higher than the user's overall diagnosis rate.

In one exemplary instance, the case order optimization tool 141 may utilize the trained system to provide an optimized case order for testing such as a general board exam or a more particular specialty exam. The trained system may optimize the case order for quality of diagnosis and/or recognition of the features that are known to be important to the diagnosis on the slides. Additionally, in the testing environment, the trained system may choose cases to be included within the case order based on a detected weakness or strength of user. Alternatively, the trained system may provide an even dispersion of topics or a select set of topics, while using new slides for all test takers.

Generally, the training phase detailed in steps 502-504 of method 500 may incorporate any training systems discussed in other embodiments herein (e.g., FIG. 3A and FIG. 4A). At step 502, the trained system may receive datasets that include pathogen slides that have previously been analyzed by either a user, pathologist, and/or AI to identify a diagnosis and/or characteristics of interest, among other examples. The diagnosis and/or characteristics data may be received along with the slides. That is, the datasets may be annotated or labeled datasets. Additionally, any of the datasets received at step 302 of method 300 discussed with reference to FIG. 3A may also be received at step 502. Optionally, the datasets may further include information from the viewing application tool 108 tracking how users are navigating the slide. For example, the tracking data may include measurements of how long a user examines the particular slides, utilization of using or not using shortcuts/hotkeys as often, and/or certain periods of staring, etc.

In some examples, the trained system may categorize the received pathogen slides by subject matter categories and subcategories. The training slides may be labeled by subject matter category or subcategory when provided as input to the system.

At step 504, the system may be trained using one or more of the datasets. For example, the system may utilize the AI-evaluated images and/or the received datasets to train the system to be configured to determine a case order that optimizes one or more of a plurality of variables given one or more constraints in an educational setting. For example, the system may be trained at step 504 similar to step 304, except for the variables optimized may be different. For example, in the educational setting, the one or more variables optimized may be improvement of qualities of diagnosis in one or more fields of pathology. In another example, the optimized variables may be an improvement in salient region identification, maximizing improvement in correct diagnosis determination, and/or maximizing improvement in pathologist efficiency. As previously discussed in detail with reference to FIG. 2, the trained system may be a trained ML system or may apply rule-based logic depending on the optimization FIG. 5B is a flowchart illustrating an example method for using a trained system to determine case order optimization in an educational context, according to one or more exemplary embodiments herein. The exemplary method 550 (e.g., steps 552-558) of FIG. 5B depicts steps that may be performed by, for example, the case order optimization tool 141. These steps may be performed automatically or in response to a request from a user (e.g., a pathologist, a department or laboratory manager, an administrator, etc.). Alternatively, the method 550 may be performed by any computer process system capable of receiving image inputs such as device 700 and capable of storing and executing the trained system described in FIG. 5A.

Generally, the method 550 may incorporate any of the steps or features discussed in other embodiments herein (e.g., FIG. 3B or FIG. 4B). At step 502, the trained system may receive a plurality of electronic medical images of pathology slides associated with pathology cases. These slides may already be pre-labeled to identify the type of pathology (e.g., a diagnosis) and areas of interest. In another example, the received electronic images of pathology slides may correspond to and be the same type of slides as described for case images 205 from FIG. 2.

At step 554, the trained system may receive any variable data 202 and constraint data 204. For example, variable data 202 may be related to training such as identifying areas for improvement or improving accuracy. Additionally, the constraint data 204 may include amounts of time that a particular user may have to study, train, or take a board/exam. Additionally, further variable 202 data and constraint data 204 may be provided to the trained system and/or kept track of by the case order optimization tool 141 while the tissue viewing platform 100 is in use.

At step 556, the trained system may determine one or more sequential orders of the pathology cases for review by one or more users in an educational setting (e.g., by one or more pathologists in training or students). In some examples, in the educational setting or context, the case order may be optimized for maximizing improvement in salient region identification, maximizing improvement in correct diagnosis determination, and/or maximizing improvement in pathologist efficiency. These variables 202 may be selected by a user/administrator, or already set as preferred variables 202 to be optimized in the educational context.

At step 558, the trained system may output the determined sequential orders of the pathology cases for review by one or more pathologists (e.g., within a list). In some examples, and as described in greater detail with reference to process 210 of FIG. 2, the electronic medical images for each case may be automatically displayed (e.g., auto-navigated to) according to the sequential order.

Optionally, the case order optimization tool 141 might prompt a break for a user. For example, the system may provide an alert when educational goals (e.g., constraints 204) for the day may be met. The case order optimization tool 141 may keep track of total training hours and user accuracy overall and within certain categories or subcategories. Further, the case order optimization tool 141 may automatically map the individual performance and feed the data to the trained system, which may be used to re-train the system at predetermined time intervals/events. This may include, taking user data from a training or testing session in which the cases are presented in the determined order to the user and feeding it back to the trained system that is then used to re-train the system to be better optimized at the outset with the next user and/or for any particular user.

In one example, the trained system may be implemented to determine an optimized case order for training one or more individuals a particular specialty within pathology, such as identifying what grade of tumor is located on a particular slide. In this case, the training datasets from step 502 and received medical images from step 552 may include various slides with different grades of tumor. Further, the training data and/or inserted medical images from step 552 may be labeled to show the location and grade of the tumor. The case order optimization tool 141 may output various slides with different grades of tumors located on them to a user in accordance with an optimized case order determined by the trained system. As a user progresses (e.g., analyzes more slides), the case order optimization tool 141 may identify what grades of tumor that the user is correctly identifying and what types that the user is not correctly identifying. The case order optimization tool 141 may provide this information to the trained system, and the trained system may proceed to update the optimized case order to give the user more cases with tumor grades that the user has failed to identify at a higher rate. This case order optimization tool 141 may continue to output cases having these certain grades of tumor until a user identifies certain grades of tumors at a predetermine accuracy percentage.

FIG. 6 is a flowchart illustrating an example method 600 for optimizing the order of cases displayed to one or more users. At step 602, a plurality of variables and one or more constraints may be received. At step 604, a plurality of pathology cases may be received. Each case of the plurality of pathology cases may include one or more medical images of at least one pathology specimen associated with a patient.

At step 606, one or more medical images from each case, the plurality of variables, and the one or more constraints may be input to a trained system. As discussed herein, the trained system may be a trained machine learning system. For example, the trained machine learning system may use dependency constraints and a constraint solver to provide slides in dependency order, as opposed to a scoring system that ranks all possible orderings.

At step 608, a sequential order for user review of the plurality of cases may be received. This order may be used to optimize one or more of the plurality of variables based on the one or more constraints. At step 610, each case of the plurality of cases may be automatically provided to a user for review, according to the sequential order.

Figure 7:
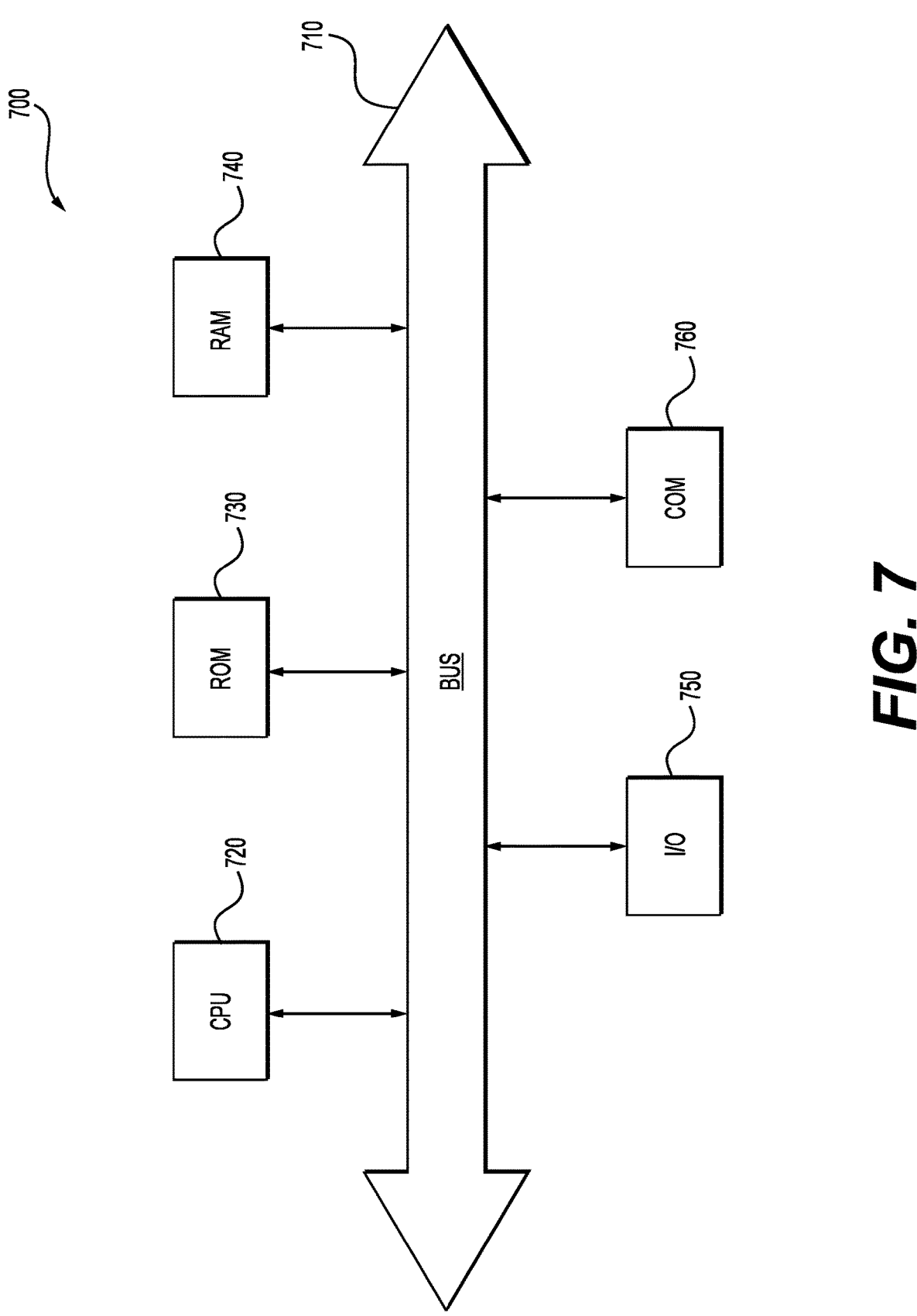
FIG. 7 depicts an example of a computing device that may execute techniques presented herein, according to one or more embodiments.

As shown in FIG. 7, device 700 may include a central processing unit (CPU) 720. CPU 720 may be any type of processor device including, for example, any type of special purpose or a general-purpose microprocessor device. As will be appreciated by persons skilled in the relevant art, CPU 720 also may be a single processor in a multi-core/multi-processor system, such system operating alone, or in a cluster of computing devices operating in a cluster or server farm. CPU 720 may be connected to a data communication infrastructure 710, for example a bus, message queue, network, or multi-core message-passing scheme.

Device 700 may also include a main memory 740, for example, random access memory (RAM), and also may include a secondary memory 730. Secondary memory 730, for example a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 730 may include similar means for allowing computer programs or other instructions to be loaded into device 700. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 700.

Device 700 also may include a communications interface ("COM") 760. Communications interface 760 allows software and data to be transferred between device 700 and external devices. Communications interface 760 may include a modem, a network interface (such as an Ethernet card), a communications port, a PCMCIA slot and card, or the like. Software and data transferred via communications interface 760 may be in the form of signals, which may be electronic, electromagnetic, optical or other signals capable of being received by communications interface 760. These signals may be provided to communications interface 760 via a communications path of device 700, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Device 700 may also include input and output ports 650 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically may be grouped together to perform a function or group of related functions. Like reference numerals are generally intended to refer to the same or similar components. Components and/or modules may be implemented in software, hardware, or a combination of software and/or hardware.

The tools, modules, and/or functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments may be apparent to those skilled in the art from consideration of the specification and practice of the invention disclosed herein. It is intended that the specification and examples be considered as exemplary only.

What is claimed is:

1. A computer-implemented method for processing electronic medical images to optimize a review order of pathology cases, comprising:

receiving a plurality of variables and one or more constraints, wherein:

the plurality of variables including at least one of a pathologist preference, a number of cases to be reviewed per day, pathologist expertise, a diagnosis quality, a time of day, a day of week, pathologist behavior, a client expectation, and a laboratory consideration, and the one or more constraints including at least one of pathologist availability, pathologist qualifications, a case deadline, a time available, and a department goal;

receiving a plurality of pathology cases, each case of the plurality of pathology cases including one or more medical images of at least one pathology specimen associated with a patient;

providing the one or more medical images from each case, the plurality of variables, and the one or more constraints as inputs to a trained machine learning system, wherein:

the plurality of variables are bounded by the one or more constraints, and the trained machine learning system having been trained to predict a sequential order for user review of the plurality of pathology cases based on a plurality of medical images, a plurality of training variables, and a plurality of training constraints;

receiving, as an output of the trained machine learning system, the sequential order for user review of the plurality of pathology cases; and automatically providing each case of the plurality of pathology cases to a user for review according to the sequential order.

2. The computer-implemented method of claim 1, wherein the trained machine learning system determines a plurality of potential sequential orders and a score for each of the plurality of potential sequential orders indicating a level of optimization of the plurality of variables, and wherein the sequential order provided as the output is one of the plurality of potential sequential orders having a highest score.

3. The computer-implemented method of claim 2, wherein when at least a first variable and a second variable of the plurality of variables are to be optimized, the trained machine learning system determines a first score for the first variable and a second score for the second variable for each of the plurality of potential sequential orders, and the sequential order provided as the output is one of the plurality of potential sequential orders having a maximized overall score based on the first score and the second score.

4. The computer-implemented method of claim 1, wherein the plurality of variables to be optimized are user-selected variables.

5. The computer-implemented method of claim 1, wherein the trained machine learning system is a trained rules-based system.

6. The computer-implemented method of claim 1, further comprising:

receiving, as a further output from the trained machine learning system, one or more determined characteristics of the one or more medical images, the trained machine learning system having been further trained to process the one or more medical images from each case of the plurality of pathology cases to determine one or more characteristics of the one or more medical images; and providing the one or more determined characteristics of the one or more medical images as a further input to the trained machine learning system, the one or more determined characteristics including a case complexity, a case type, a number of areas of interest per medical image or per case, an amount of tissue per medical image, or an image quality.

7. The computer-implemented method of claim 1, further comprising:

receiving one or more additional pathology cases, each case of the one or more additional pathology cases including the one or more medical images of the at least one pathology specimen associated with the patient;

providing the one or more medical images from each of the one or more additional pathology cases as a further input to the trained machine learning system; and receiving, as the output of the trained machine learning system, an updated sequential order.

8. The computer-implemented method of claim 1, wherein the trained machine learning system is further configured to assign a subset of the plurality of pathology cases to each of a plurality of users.

9. The computer-implemented method of claim 1, further comprising:

generating a notification to prompt the user to take one or more breaks to increase optimization of the plurality of variables or the one or more constraints based on information received from the trained machine learning system.

10. The computer-implemented method of claim 1, wherein automatically providing each case of the plurality of pathology cases to the user for review according to the sequential order comprises:

automatically navigating from an initial case to a subsequent case according to the sequential order based on an indication that a review of the initial case is completed.

11. The computer-implemented method of claim 10, wherein the indication is an input received from the user or an event associated with case review completion that is automatically detected.

12. The computer-implemented method of claim 1, further comprising:

monitoring for values associated with the plurality of variables as the user is reviewing the plurality of pathology cases; and providing the values to the trained machine learning system, wherein the trained machine learning system is re-trained based on the values for future optimizations.

13. A system for processing electronic medical images, the system comprising:

at least one memory storing instructions; and at least one processor configured to execute the instructions to perform operations comprising:

receiving a plurality of variables and one or more constraints, wherein the plurality of variables are bounded by the one or more constraints;

receiving a plurality of pathology cases, each case of the plurality of pathology cases including one or more medical images of at least one pathology specimen associated with a patient;

providing the one or more medical images from each case, the plurality of variables, and the one or more constraints as input to a trained machine learning system, the trained machine learning system having been trained to predict a sequential order for user review of the plurality of pathology cases based on a plurality of medical images, a plurality of training variables, and a plurality of training constraints;

receiving, as an output of the trained machine learning system, the sequential order for user review of the plurality of pathology cases; and automatically providing each case of the plurality of pathology cases to a user for review according to the sequential order.

14. The system of claim 13, wherein the trained machine learning system determines a plurality of potential sequential orders and a score for each of the plurality of potential sequential orders indicating a level of optimization of the plurality of variables, and wherein the sequential order provided as the output is one of the plurality of potential sequential orders having a highest score.

15. The system of claim 14, wherein when at least a first variable and a second variable of the plurality of variables are to be optimized, the trained machine learning system determines a first score for the first variable and a second score for the second variable for each of the plurality of potential sequential orders, and the sequential order provided as the output is one of the plurality of potential sequential orders having a maximized overall score based on the first score and the second score.

16. The system of claim 13, wherein the plurality of variables to be optimized are user-selected variables.

17. The system of claim 13, wherein the trained machine learning system is a trained rules-based system.

18. The system of claim 13, further comprising:

receiving, as a further output from the trained machine learning system, one or more determined characteristics of the one or more medical images, the trained machine learning system having been further trained to process the one or more medical images from each case of the plurality of pathology cases to determine one or more characteristics of the one or more medical images; and providing the one or more determined characteristics of the one or more medical images as a further input to the trained machine learning system, the one or more determined characteristics including a case complexity, a case type, a number of areas of interest per medical image or per case, an amount of tissue per medical image, or an image quality.

19. A non-transitory computer-readable medium storing instructions that, when executed by a processor, perform operations processing electronic medical images, the operations comprising:

receiving a plurality of variables and one or more constraints, wherein:

the plurality of variables including at least one of a pathologist preference, a number of cases to be reviewed per day, pathologist expertise, a diagnosis quality, a time of day, a day of week, pathologist behavior, a client expectation, and a laboratory consideration, and the one or more constraints including at least one of pathologist availability, pathologist qualifications, a case deadline, a time available, and a department goal;

receiving a plurality of pathology cases, each case of the plurality of pathology cases including one or more medical images of at least one pathology specimen associated with a patient;

providing the one or more medical images from each case, the plurality of variables, and the one or more constraints as inputs to a trained machine learning system, wherein:

the plurality of variables are bounded by the one or more constraints, and the trained machine learning system having been trained to predict a sequential order for user review of the plurality of pathology cases based on a plurality of medical images, a plurality of training variables, and a plurality of training constraints;

receiving, as an output of the trained machine learning system, the sequential order for user review of the plurality of pathology cases to optimize one or more of the plurality of variables based on the one or more constraints; and automatically providing each case of the plurality of pathology cases to a user for review according to the sequential order.

20. The computer-readable medium of claim 19, wherein the trained machine learning system determines a plurality of potential sequential orders and a score for each of the plurality of potential sequential orders indicating a level of optimization of the plurality of variables, and wherein the sequential order provided as the output is one of the plurality of potential sequential orders having a highest score.

* * * * *